Figure 3E:
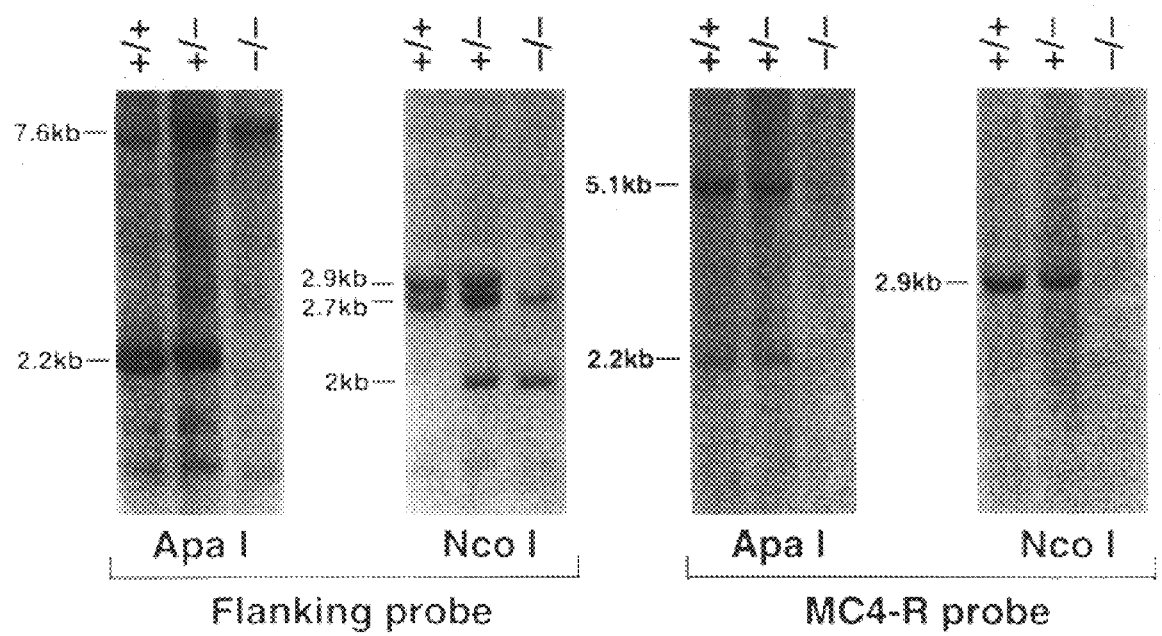

United States Patent [19]
Lee et al.

[11] Patent Number: 5,932,779
[45] Date of Patent: Aug. 3, 1999

[54] SCREENING METHODS FOR COMPOUNDS USEFUL IN THE REGULATION OF BODY WEIGHT

[75] Inventors: Frank Lee, Chestnut Hill; Dennis Huszar, Acton; Wei Gu, Brookline, all of Mass.

[73] Assignee: Millennium Pharmaceuticals, Inc., Cambridge, Mass.

[21] Appl. No.: 08/780,749

[22] Filed: Jan. 8, 1997

Related U.S. Application Data

[63] Continuation-in-part of application No. 08/662,560, Jun. 10, 1996.
[51] Int. Cl.$^6$ .............................. C12N 15/00; C12N 15/09
[52] U.S. Cl. ............................................. 800/2; 435/172.3
[58] Field of Search ............................. 800/2; 435/172.3; 536/23.1

[56] References Cited

FOREIGN PATENT DOCUMENTS

WO 98/10068   3/1998   WIPO .

OTHER PUBLICATIONS

Xue, B. et al., 1997, "The agouti gene product stimulates pancreatic beta cell $Ca^{2+}$ signaling and insulin release", FASEB Journal 11(3):A230.

Zemel, M.B. et al., 1997, "Agouti regulation of leptin expression in adipocytes", FASEB Journal 11(3):A352.

Mynatt, R.L., 1997, "Combined effects of insulin treatment and adipose tissue–specific agouti expression on the development of obesity", PNAS USA 94:919–922.

Boston, B.A. & Cone, R.D., 1996, "Characterization of Melanocortin Receptor Subtype Expression in Murine Adipose Tissues and in the 3T3–L1 Cell Line", Endocron. 137(5):2043–2050.

Boston, B.A. & Cone, R.D., 1996, "Induction of Melanocortin Receptor (MC2–R & MC–R) Expression During Adipocyte Differentiation in the 3T3–L1 Cell Line and Distribution of Expression in Mature Adipose Tissues", Inst. Adv. Biomed. Res. (abstract) 103A.

Cone, R.D. et al., 1996, "The Melanocortin Receptors: Agonists, Antagonists, and the Hormonal Control of Pigmentation", Recent progress in Hormone Res. 51:287–319.

Zemel, M.B. et al., 1996, "Agouti–Induced Obesity is not Antagonized by the Melanocortin Receptor Agonist, NDP–MSH", Obesity Research 4(1):45S.

Manne, J. et al., 1995, "Mechanisms for the pleiotropic effects of the agouti gene", PNAS USA 92:4721–4724.

Willard, D.H., 1995, "Agouti Structure and Function: Characterization of a Potent α–Melanocyte Stimulating Hormone Receptor Antagonist", Biochem. 34(38):12341–12346.

Zemel, M.B., 1995, "Agouti regulation of intracellular calcium: Role in the insulin resistance of viable yellow mice", PNAS USA 92:4733–4737.

Mountjoy, K.G. et al., 1994, "Localization of the Melanocortin–4 Receptor (MC4–R) in Neuroendocrine and Automatic Control Circuits in the Brain", Mol. Endocrinol. 8(10):1298–1308.

Yen, T. et al., 1994, "Obesity, diabetes, and neoplasia in yellow $A^{vy}$/–mice: ectopic expression of the agouti gene", FASEB J. 8:479–488.

Gold, R.M. et al., 1977, "Paraventricular Area: Critical Focus of a Longitudinal Neurocircuitry Mediating Food Intake", Physiol. and Behavior 18:1111–1119.

Brecher, G. et al., 1964, "The Brain Lesion of Goldthioglucose Obesity", Nat. Inst. Arthrit. Metab. Dis. pp. 395–401.

Alvaro, J.D., 1995, "Cloning of the rat melanocortin 4 receptor in brain and its regulation by opiates (locus, coeruleus, ventral tegmentum)", Doctoral Dissertation, Yale University, New Haven, CT, 116 pages.

Mauri, A. et al., 1995, "Melanocortins and opoids modulate early postnatal growth in rats", Regulatory Pep. 59:59–66.

Albanese, C. et al., 1994, "Development of a bioassay for FSH using a recombinant human FSH receptor and a cAMP responsive luciferase reporter gene", Molec. and Cell. Endocrin. 101:211–219.

Hruby et al., 1995, "Cyclic Lactam α–Melanotropin Analogues of Ac–Nle$^4$–cyclo[Asp$^5$ ,D–Phe$^7$,Lys$^{10}$]α–Melanocyte–Stimulating Hormone–(4–10)–NH$_2$ with Bulky Aromatic Amino Acids at Position 7 Show High Antagonist Potency and Selectivity at Specific Melanocortin Receptors", J. Med. Chem. 38:3454–3461.

Klebig et al., 1995, "Ectopic Expression of the Agouti Gene in Transgenic Mice Causes Obesity, Features of Type II Diabetes, and Yellow Fur", Proc. Natl. Acad. Sci. USA 92:4728–4732.

Manne et al., 1995, "Mechanisms for the Pleitropic Effects of the Agouti Gene", Proc. Natl. Acad. Sci. USA 92:4721–4724.

Perry et al., 1995, "A Transgenic Mouse Assay for Agouti Protein Activity", Genetics 140:267–274.

Adan et al., 1994, "Identification of Agonists for Melanocortin MC$^3$, MC$^4$ and MC$^5$ Receptors", Eur. J. Pharmacol. 269:331–337.

Ezzell, 1994, "How Chaperonins Monitor Their Protein Charges", J. NIH Res. 6:31–34.

Gantz et al., 1994, "Molecular Cloning, Expression, and Characterization of a Fifth Melanocortin Receptor", Biochem. and Biophys. Res. Comm. 200:1214–1220.

(List continued on next page.)

*Primary Examiner*—Brian R. Stanton
*Attorney, Agent, or Firm*—Pennie & Edmonds, LLP

[57] ABSTRACT

The present invention relates to drug screening assays, and diagnostic and therapeutic methods for the treatment of body weight disorders, such as obesity, anorexia and cachexia, utilizing the melanocortin 4-receptor (MC4-R) as the target for intervention. The invention also relates to compounds that modulate the activity or expression of the MC4-R, and the use of such compounds in the treatment of body weight disorders.

5 Claims, 19 Drawing Sheets

OTHER PUBLICATIONS

Griffon et al., 1994, "Molecular Cloning and Characterization of the Rat Fifth Melanocortin Receptor", Biochem. and Biophys. Res. Comm. 200:1007–1014.

Labbe et al., 1994, "Molecular Cloning of a Mouse Melanocortin 5 Receptor Gene Widely Expressed in Peripheral Tissues", Biochem. 33:4543–4549.

Low et al., 1994, "Receptors for the Melanocortin Peptides in the Central Nervous System", Curr. Op. in Endocrinol. and Diabetes 1994:79–88.

Lu et al., 1994, "Agouti Protein is an Antagonist of the Melanocyte–Stimulating Hormone Receptor", Nature 371:799–802.

Michaud et al., 1994, "A Molecular Model for the Genetic and Phenotypic Characteristics of the Mouse Lethal Yellow ($A^y$) Mutation", Proc. Natl. Acad. Sci. USA 91:2526–2566.

Michaud et al., 1994, "Differential Expression of a New Dominant Agouti Allele ($A^{iapy}$) is Correlated with Methylation State and is Influenced by Parental Lineage", Genes & Dev. 8:1463–1472.

Mountjoy et al., 1994, "Localization of the Melanocortin–4 Receptor (MC4–R) in Neuroendocrine and Autonomic Control Circuits in the Brain", Mol. Endocrinol. 8:1298–1308.

Siracusa, 1994, "The Agouti Gene: Turned on to Yellow", TIG 10:423–428.

Yen et al., 1994, "Obesity, Diabetes, and Neoplasia in Yellow $A^{vy}$/–Mice: Ectopic Expression of the Agouti Gene", FASEB 8:479–488.

Chhajlani et al., 1993, "Molecular Cloning of a Novel Human Melanocortin Receptor", Biochem. and Biophys. Res. Comm. 195:866–873.

Conklin and Bourne, 1993, "Mouse Coat Colour Reconsidered", Nature 364:110.

Gantz et al., 1993, "Molecular Cloning, Expression, and Gene Localization of a Fourth Melanocortin Receptor", J. Biol. Chem. 268:15174–15179.

Jackson, 1993, "Colour–Coded Switches", Nature 362:587–588.

Michaud et al., 1993, "The Embryonic Lethality of Homozygous Lethal Yellow Mice ($A^y/A^y$) Is Associated with the Disruption of a Novel RNA–Binding Protein", Genes & Dev. 7:1203–1213.

Miller et al., 1993, "Cloning of the Mouse Agouti Gene Predicts a Secreted Protein Ubiquitously Expressed in Mice Carrying the Lethal Yellow Mutation", Genes & Dev. 7:454–467.

Roselli–Rehfuss et al., 1993, "Identification of a Receptor for γMelanotropin and other Proopiomelanocortin Peptides in the Hypothalamus and Limbic System", Proc. Natl. Acad. Sci. USA 90:8856–8860.

Robbins et al., 1993, "Pigmentation Phenotypes of Variant Extension Locus Alleles Result from Point Mutations that Alter MSH Receptor Function", Cell 72:827–834.

Bultman et al., 1992, "Molecular Characterization of the Mouse Agouti Locus", Cell 71:1195–1204.

Chhajlani and Wikberg, 1992, "Molecular Cloning and Expression of the Human Melanocyte Stimulating Hormone Receptor cDNA", FEBS 309:417–420.

Mountjoy et al., 1992, "The Cloning of a Family of Genes That Encode the Melanocortin Receptors", Science 257:1248–1251.

Shimizu et al., 1989, "Effects of MSH on Food Intake, Body Weight and Coat Color of the Yellow Obese Mouse", Life Sci. 45:543–552.

Frigeri et al., 1988, "Differential Responses of Yellow $A^{vy}$/A and Agouti A/a (BALB/c x VY) F, Hybrid Mice to the Same Diets: Glucose Tolerance, Weight Gain, and Adipocyte Cellularity", Int. J. Obesity 12:305–320.

Wolff, 1987, "Body Weight and Cancer", Am. J. Clin. Nutr. 45:168–180.

Wolff et al., 1986, "Prenatal Determination of Obesity, Tumor Susceptibility, and Coat Color Pattern in Viable Yellow ($A^{vy}$/a) Mice", J. Heredity 77:151–158.

Wolff et al., 1978, "Phaeomelanin Synthesis and Obesity in Mice", J. Heredity 69:295–298.

Yen et al., 1976, "An Analysis of the Relationships Among Obesity, Plasma Insulin, and Hepatic Lipogenic Enzymes in 'Viable Yellow Obese' ($A^{vy}$/a)", Horm. Metab. Res. 8:159–166.

Yen et al., 1976, "Triacylglycerol Contents and In Vivo Lipogenesis of Ob/Ob, Db/Db and $A^{vy}$/a Mice", Biochimica et Biophysica Acta 441:213–220.

Johnson and Hirsch, 1972, "Cellularity of Adipose Depots in Six Strains of Genetically Obese Mice", J. Lipid Res. 13:2–11.

Yen et al., 1970, "Lipolysis in Genetically Obese and Diabetes–Prone Mice", Horm. metab. Res. 2:200–203.

Searle, 1968, "An Extension Series in the Mouse", J. Heredity 59:341–342.

Castle, 1940, "Influence of Certain Color Mutations on Body Size in Mice, Rats, and Rabbits", Genetics 26:177–191.

Bradley et al., 1992 Biotechnology 10:534–539.

Robbins et al., 1993. Cell 72:827–834.

Detloff et al. 1994. Molecular and Cellular Biology 14(10):6936–6943.

Klebig et al., 1995. Proceedings of the National Academy of Science, USA 92:4728–4732.

```
                    ECD 1                                                    50
     1    MSIQKKYLEG DFVFPVSSSS FLRTLLEPQL GSALLTAMNA SCCLPSVQPT
MC3
MC4       .......... .......... .......... .MVNSTHRGM HTSLHLWNRS SYRLHS....
MC2(ACTH) .......... .......... .......... .......... .......... .....MKH
MC1(α-MSH) .......... .......... .......... .......... ......MAV QGSQRRLLGS

I              100
    51    LPNGSEHLQA PFFSNQSSSA FCEQVFIKPE IFLSLGIVSL LENILVILAV
MC3
MC4       ..NASESLGK GY....SDGG CYEQLFVSPE VFVTLGVISL LENILVIVAI
MC2(ACTH) IINSYENINN T....ARNNS DCPRVVLPEE IFFTISIVGV LENLIVLLAV
MC1(α-MSH) LNSTPTAIPQ LGLAANQTGA RCLEVSISDG LFLSLGIVSL VENALVVATI

CD 1               II                ECD 2         150
   101    VRNGNLHSPM YFFLCSLAVA DMLVSVSNAL ETIMIAIVHS DYLTFEDQFI
MC3
MC4       AKNKNLHSPM YFFICSLAVA DMLVSVSNGS ETIITLLNS T.DTDAQSFT
MC2(ACTH) FKNKNLQAPM YFFICSLAIS DMLGSLYKIL ENILIIRNM GYLKPRGSFE
MC1(α-MSH) AKNRNLHSPM YCFICCLALS DLLVSGTNVL ETAVILILEA GALVARAAVL

III                       CD 2                   200
   151    QHMDNIFDSM ICISLVASIC NLLAIAVDRY VTIFYALRYH SIMTVRKALT
MC3
MC4       VNIDNVIDSV ICSSLLASIC SLLSIAVDRY FTIFYALQYH NIMTVKRVGI
MC2(ACTH) TTADDIIDSL FVLSLLGSIF SLSVIAADRY ITIFHALRYH SIVIMRRTVV
MC1(α-MSH) CQLDNVIDVI TCSSMLSSLC FLGAIAVDRY ISIFYALRYH SIVTLPRARQ
```

FIG. 1A

```
                    IV                        ECD 3                      V        250
201      LIVAIWCCG  VCGVVFIVYS  ESKMVIVCLI  TMFFAMMLLM  GTLYVHMFLF
MC 3     IISCIWAACT  VSGILFIYS  DSSAVIICLI  TMFFTMLALM  ASLYVHMFLM
MC 4     VLTVIWTFCT  GTGITMVIFS  HHVPIVITFT  SLFPLMLVFI  LCLYVHMFLL
MC 2 (ACTH)
MC 1 (α-MSH)  AVAAIWVASV  VFSTLFIAYY  DHVAVLLCLV  VFFLAMLVLM  AVLYVHMLAR

ECD 4         3i                                VI      300
251      ARLHVKRIAA  LPPADGVAPQ  QHSCMKGAVT  ITILLGVFIF  CWAPFFLHIV
MC 3     ARLHIKRIAV  LPGTGAI..R  QGANMKGAIT  LTILIGVFVV  CWAPFFLHLI
MC 4     ARSHTRKIST  LPR.......  ..ANMKGAIT  LTILLGVFIF  CWAPFVLHVL
MC 2 (ACTH)
MC 1 (α-MSH)  ACQHAQGIAR  LHKRQ.R.PVH  QGFGLKGAVT  LTILLGIFFL  CWGPFFLHLT

ECD 4                           VII              CD 4    350
301      LIITCPTNPY  CICYTAHFNT  YLVLIMCNSV  IDPLIYAFRS  LELRNTFREI
MC 3     FYISCPQNPY  CVCFMSHFNL  YLILIMCNSI  IDPLIYALRS  QELRKTFKEI
MC 4     LMTFCPSNPY  CACYMSLFQV  NGMLIMCNAV  IDPFIYAFRS  PELRDAFKKM
MC 2 (ACTH)
MC 1 (α-MSH)  LIVLCPEHPT  CGCIFKNFNL  FLALIICNAI  IDPLIYAFHS  QELRRTLKEV

351      LCGCNGMNLG
MC 3     ICCYPLGGLC  DLSSRY
MC 4     IFCSRYW
MC 2 (ACTH)
MC 1 (α-MSH)  LTCSW
```

FIG. 1B

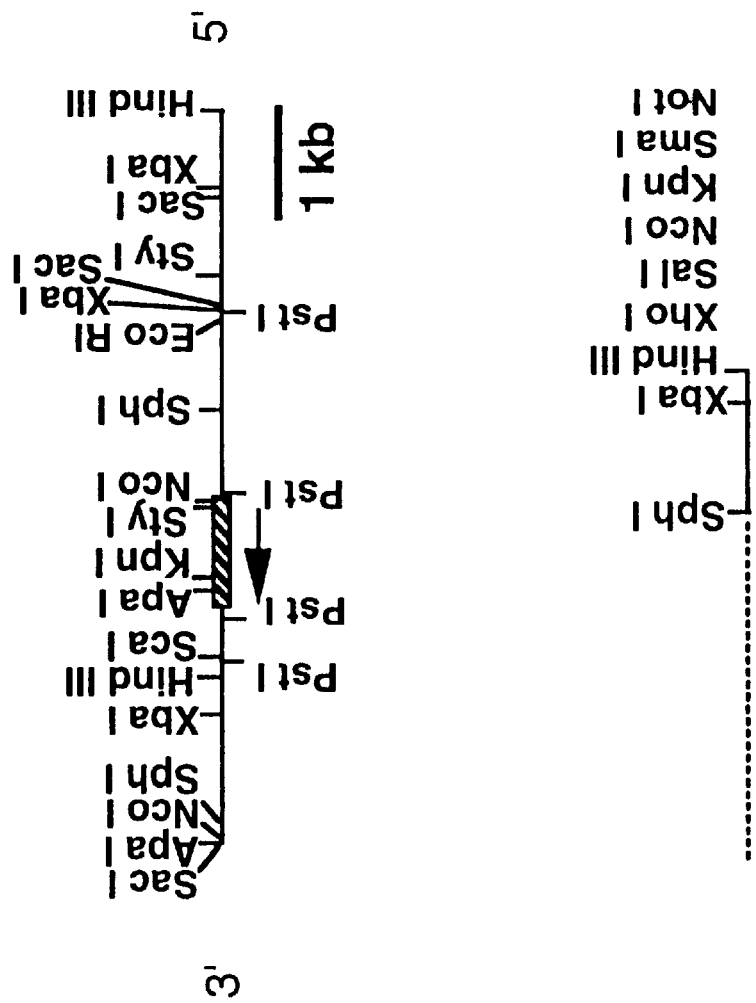
FIG. 2A  MC4-R locus
FIG. 2B  MC4-R KO 5'

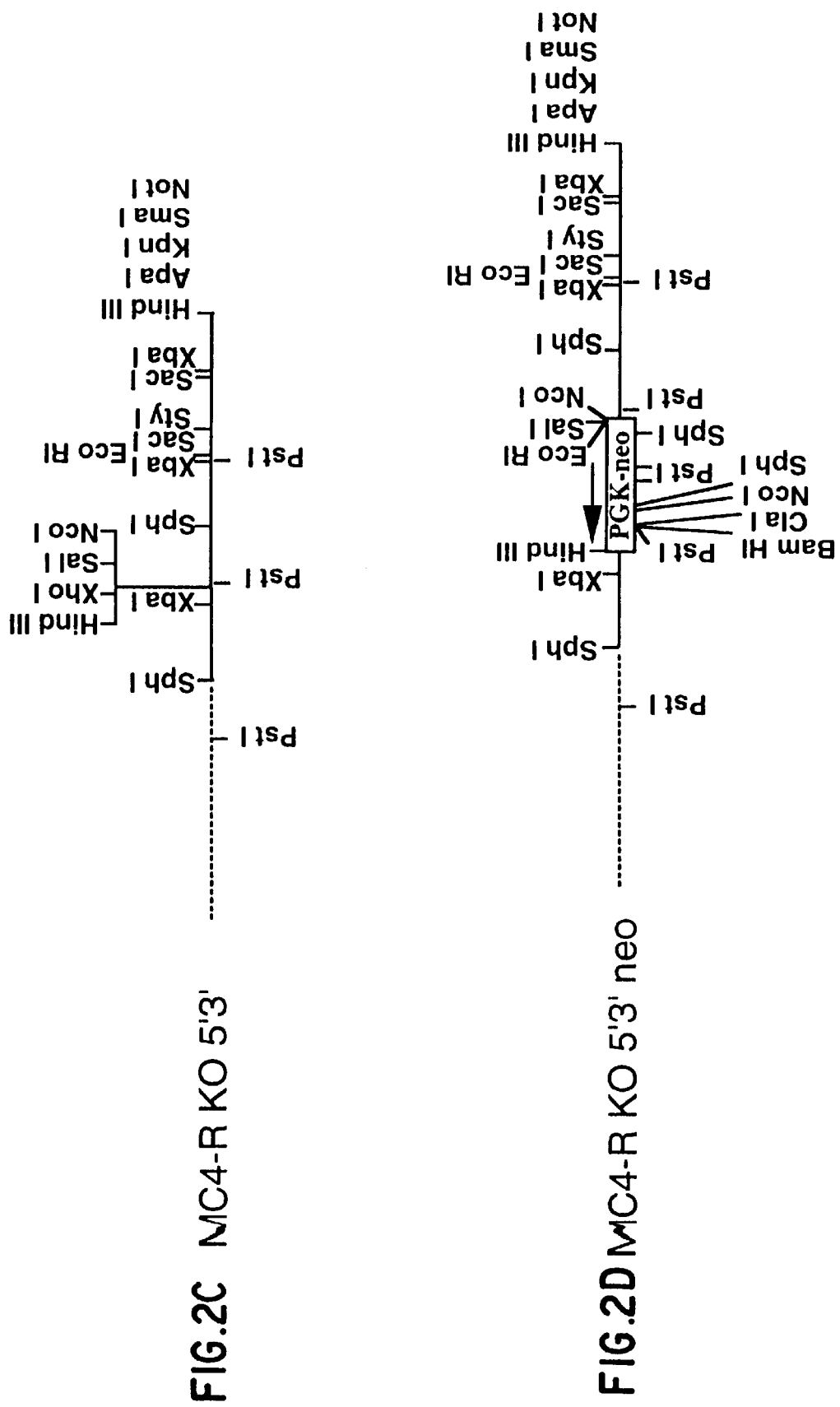
FIG.2C MC4-R KO 5'3'
FIG.2D MC4-R KO 5'3' neo

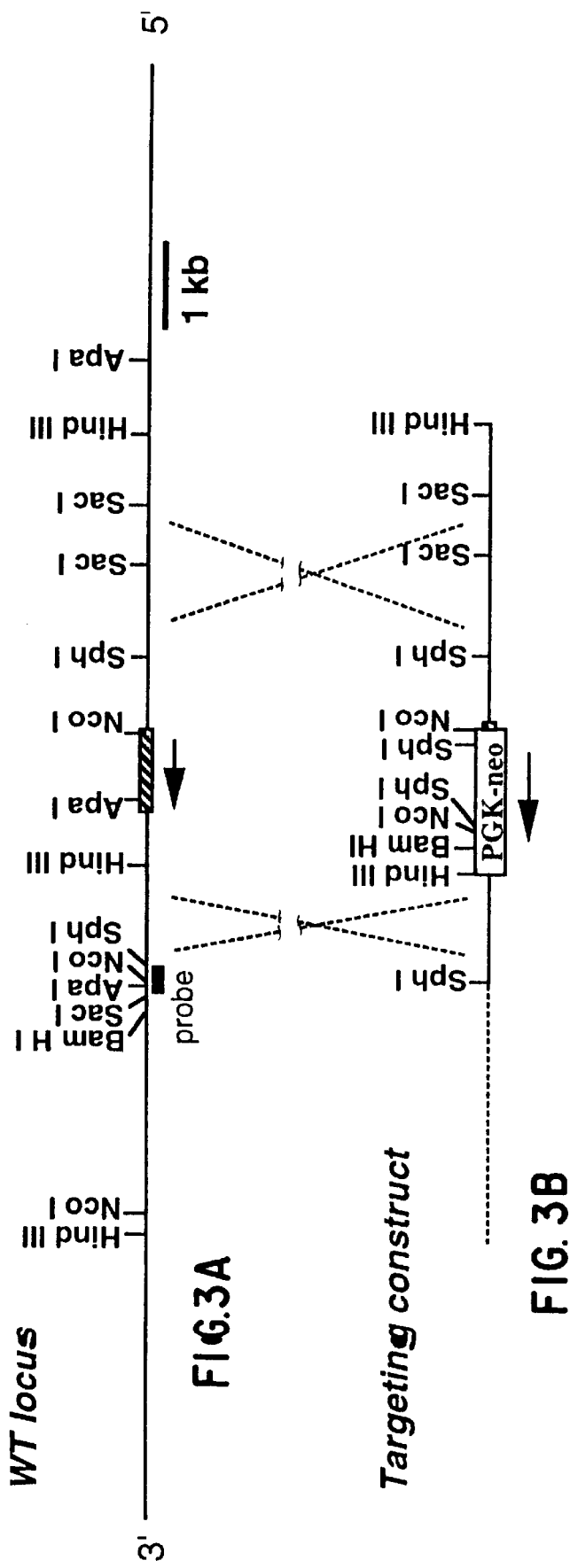

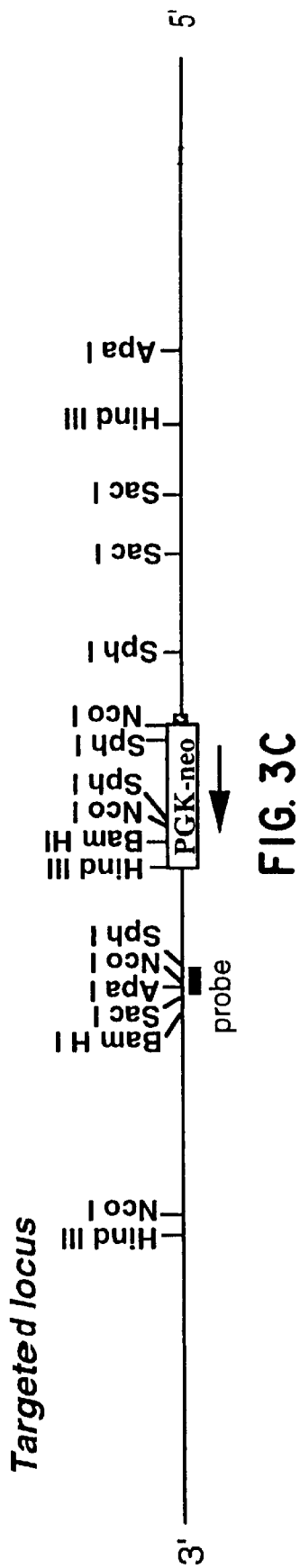

```
AGC TTC CGA GAG GCA GCC GAT GTG AGC ATG TGC GCA CAG ATT CGT CTC CCA ATG  -340
GCA TGG CAG CTT CAA GGA AAA TTA TTT TGA ACA GAC TTG AAT GCA TAA GAT TAA  -286
AGT TAA AGC AGA AGT GAG CCC AAG ATT TTA AAG TGA TGA TTA GAG CTC AGA AGA  -232
ATG AAT ATT TTG AAG ACC TCC ATG TCA AGC TCT GGA CTT GTG ACA TTT CAC CTA  -178
AAA GAG ACT AAA AAC TTT AGC CTC ACA ACT TTC AGA CAG ATA AAG ACT TGG AGC  -124
AGG CAT GGC AAT TTT AGC CTC CCT GAC CTC AGA GGT TAA ATC AAT TCA GGG AAA   -70
TAA CTG AGA CGA CTC CCT GAC CTC AGA GGT TAA ATC AAT TCA GGG GGA CAC TGG   -16

AAT TCT CCT GCC AGC ATG GTG AAC TCC ACC CAC CGT GGG ATG CAC ACT TCT CTG   39
                    MET Val Asn Ser Thr His Arg Gly MET His Thr Ser Leu   13

CAC CTC TGG AAC CGC AGC AGT TAC AGA CTG CAC AGC AAT GCC AGT GAG TCC CTT   93
His Leu Trp Asn Arg Ser Ser Tyr Arg Leu His Ser Asn Ala Ser Glu Ser Leu   31

GGA AAA GGC TAC TCT GAT GGA GGG TGC TAC GAG CAA CTT TTT GTC TCT CCT GAG  147
Gly Lys Gly Tyr Ser Asp Gly Gly Cys Tyr Glu Gln Leu Phe Val Ser Pro Glu   49
                                        I

GTG TTT GTG ACT CTG GGT GTC ATC AGC TTG TTG GAG AAT ATC TTA GTG ATT GTG  201
Val Phe Val Thr Leu Gly Val Ile Ser Leu Leu Glu Asn Ile Leu Val Ile Val   67

GCA ATA GCC AAG AAC AAG AAT CTG CAT TCA CCC ATG TAC TTT TTC ATC TGC AGC  255
Ala Ile Ala Lys Asn Lys Asn Leu His Ser Pro MET Tyr Phe Phe Ile Cys Ser   85
                                        II

TTG GCT GTG GCT GAT ATG CTG GTG AGC GTT TCA AAT GGA TCA GAA ACC ATT ATC  309
Leu Ala Val Ala Asp MET Leu Val Ser Val Ser Asn Gly Ser Glu Thr Ile Ile  103
                                                        Val Ser    Val
```

FIG. 5A

```
ATC ACC CTA TTA AAC AGT ACA GAT ACG GAT GCA CAG AGT TTC ACA GTG AAT ATT 363
Ile Thr Leu Leu Asn Ser Thr Asp Thr Asp Ala Gln Ser Phe Thr Val Asn Ile 121
                                          III

GAT AAT GTC ATT GAC TCG GTG ATC TGT AGC TCC TTG CTT GCA TCC ATT TGC AGC 417
Asp Asn Val Ile Asp Ser Val Ile Cys Ser Ser Leu Leu Ala Ser Ile Cys Ser 139

CTG CTT TCA ATT GCA GTG GAC AGG TAC TTT ACT ATC TTC TAT GCT CTC CAG TAC 471
Leu Leu Ser Ile Ala Val Asp Arg Tyr Phe Thr Ile Phe Tyr Ala Leu Gln Tyr 157

CAT AAC ATT ATG ACA GTT AAG CGG GTT GGG ATC AGC ATA AGT TGT ATC TGG GCA 525
His Asn Ile MET Thr Val Lys Arg Val Gly Ile Ser Ile Ser Cys Ile Trp Ala 175
                                      Arg                  Ile
                                     IV

GCT TGC ACG GTT TCA GGC ATT TTG CTT TTC ATC ATT TAC TCA GAT AGT AGT GCT GTC 579
Ala Cys Thr Val Ser Gly Ile Leu Phe Ile Ile Tyr Ser Asp Ser Ser Ala Val 193
                         Val

ATC ATC TGC CTC ATC ACC ATG TTC TTC ACC ATG CTG GCT CTC ATG GCT TCT CTC 633
Ile Ile Cys Leu Ile Thr Met Phe Phe Thr MET Leu Ala Leu MET Ala Ser Leu 211
                             Val

TAT GTC CAC ATG TTC CTG ATG GCC AGG CTT CAC ATT AAG AGG ATT GCT GTC CTC 687
Tyr Val His MET Phe Leu MET Ala Arg Leu His Ile Lys Arg Ile Ala Val Leu 229

CCC GGC ACT GGT GCC ATC CGC CAA GGT GCC AAT ATG AAG GGA GCG ATT ACC TTG 741
Pro Gly Thr Gly Ala Ile Arg Gln Gly Ala Asn MET Lys Gly Ala Ile Thr Leu 247
                                                        Thr
```

FIG. 5B

FIG. 5C

```
                          VI
ACC ATC CTG ATT GGC GTC TTT GTT GTC TGC TGG GCC CCA TTC TTC CTC CAC TTA  795
Thr Ile Leu Ile Gly Val Phe Val Val Cys Trp Ala Pro Phe Phe Leu His Leu  265

ATA TTC TAC ATC TCT TGT CCT CAG AAT CCA TAT TGT GTG TGC TTC ATG TCT CAC  849
Ile Phe Tyr Ile Ser Cys Pro Gln Asn Pro Tyr Cys Val Cys Phe MET Ser His  283
Leu
                                              VII
TTT AAC TTG TAT CTC ATA CTG ATC ATG TGT AAT TCA ATC ATC GAT CCT CTG ATT  903
Phe Asn Leu Tyr Leu Ile Leu Ile MET Cys Asn Ser Ile Ile Asp Pro Leu Ile  301

TAT GCA CTC CGG AGT CAA GAA CTG AGG AAA ACC TTC AAA GAG ATC TGT TGC      957
Tyr Ala Leu Arg Ser Gln Glu Leu Arg Lys Thr Phe Lys Glu Ile Cys Cys      319

TAT CCC CTG GGA GGC CTT TGT GAC TTG TCT AGC AGA TAT TAA ATG GGG ACA GAG  996
Tyr Pro Leu Gly Gly Leu Cys Asp Leu Ser Ser Arg Tyr                      332

CAC GCA ATA TAG GAA CAT GCA CTT TCA CTC TTA CCC TAC CTG AAT              1050
ATT GTA CTT CTG CAA CAG CTT TCT CTT CCG GTA CTG GAG ATA TCC              1108
ATT GTG TAA ATT TAA GCC TAT GAT TTT TAA TGA AAA ATG CCC AGT CTC TGT      1162
ATT ATT TCC AAT GTC ATG CTA CTT TTT TGG CCA TAA AAT AAT ATG TAT          1216
AGG TTG TAG GCA CTG TGG ATT TAC AAA AAG AGT CCT TAT TAA AAG CTT          1267
```

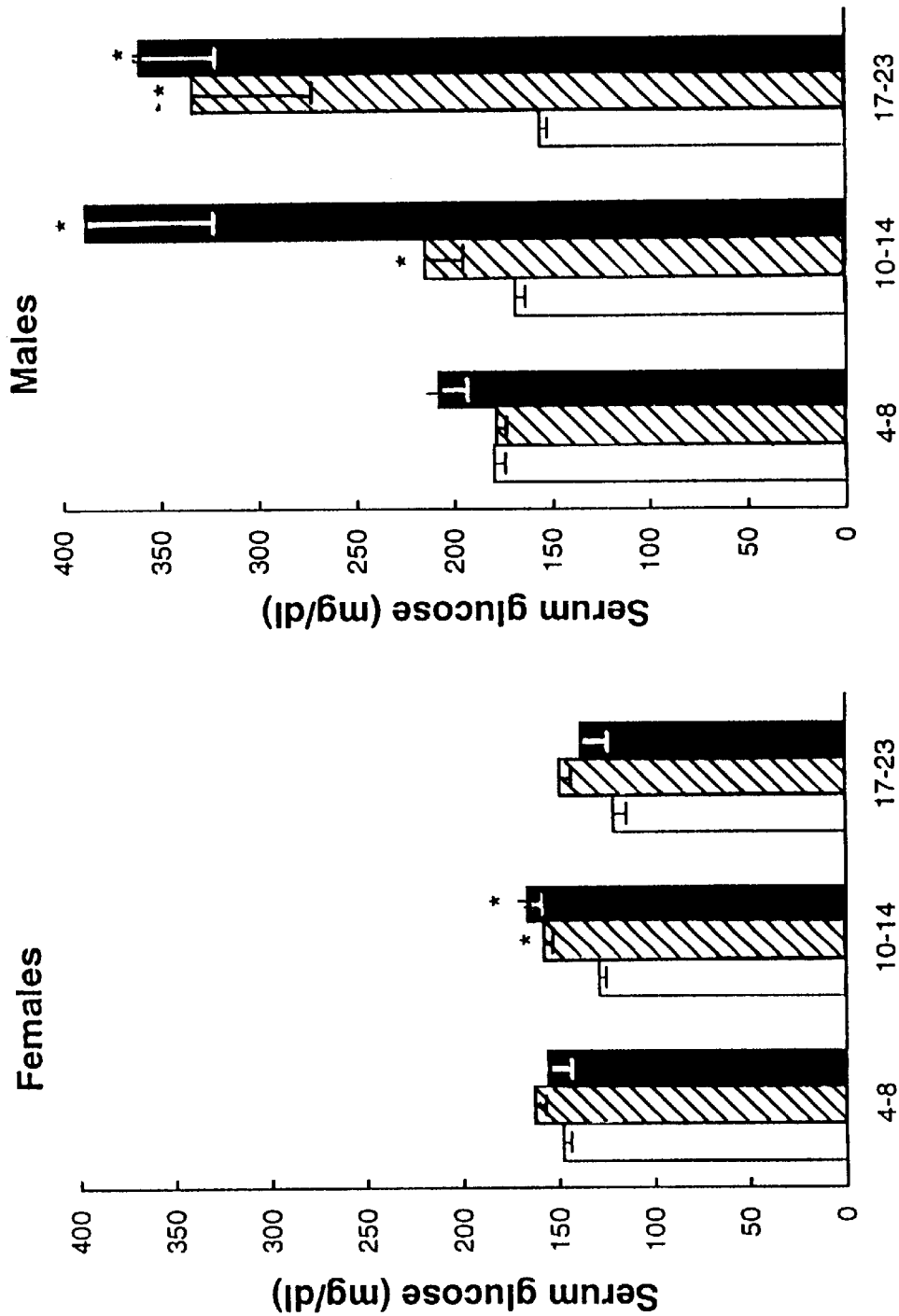

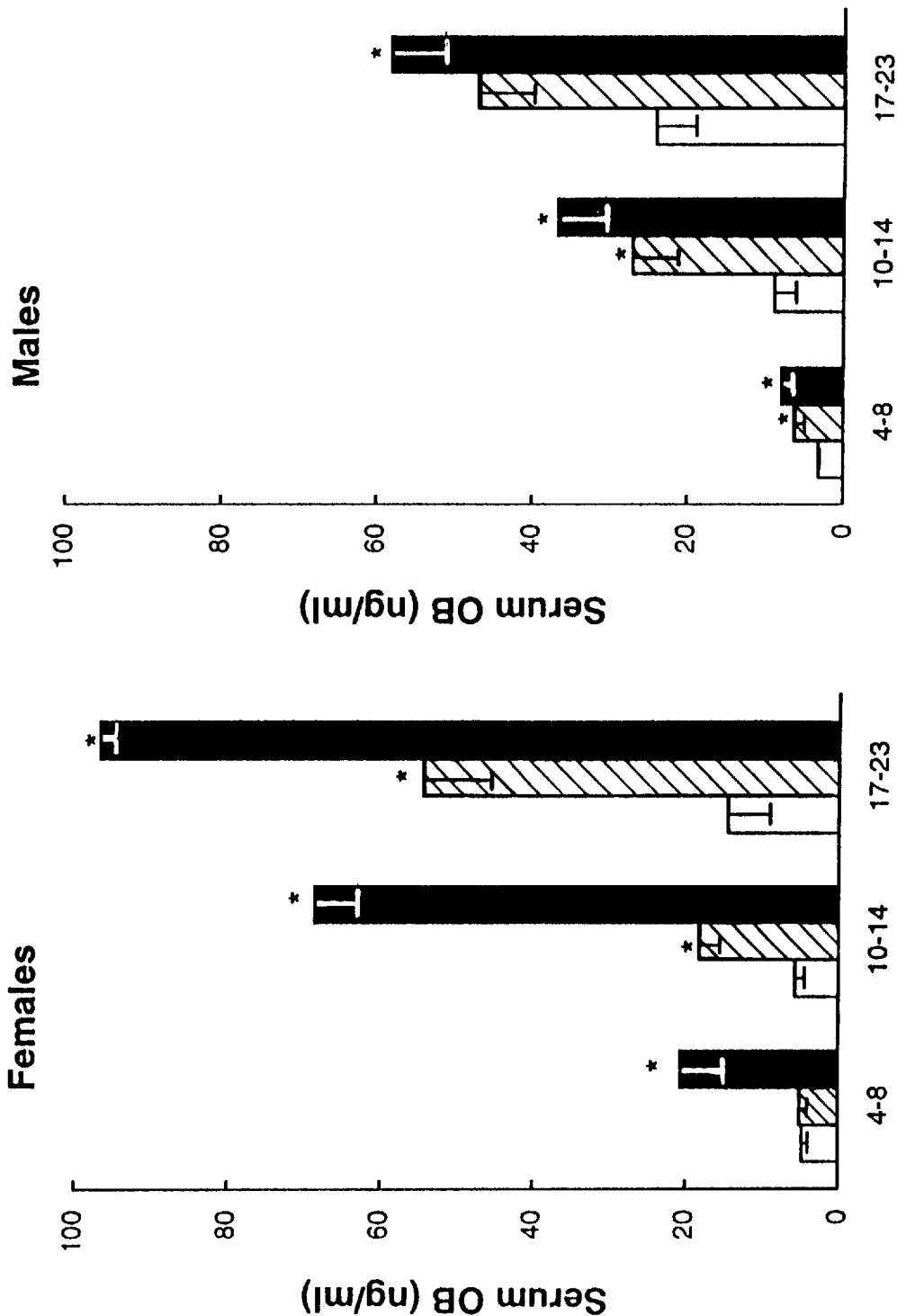

SCREENING METHODS FOR COMPOUNDS USEFUL IN THE REGULATION OF BODY WEIGHT

This application is a continuation-in-part of application Ser. No. 08/662,560 filed Jun. 10, 1996.

TABLE OF CONTENTS
1. INTRODUCTION
2. BACKGROUND OF THE INVENTION
   2.1. THE MELANOCORTIN RECEPTORS
   2.2. THE AGOUTI PROTEIN
3. SUMMARY OF THE INVENTION
   3.1. DEFINITIONS
4. DESCRIPTION OF THE FIGURES
5. DETAILED DESCRIPTION OF THE INVENTION
   5.1. THE ROLE OF MC4-R IN THE REGULATION OF BODY WEIGHT
   5.2. SCREENING ASSAYS FOR DRUGS USEFUL IN REGULATION OF BODY WEIGHT
      5.2.1. CELL-BASED ASSAYS
      5.2.2. NON-CELL BASED ASSAYS
      5.2.3. ASSAYS FOR COMPOUNDS OR COMPOSITIONS THAT MODULATE EXPRESSION OF THE MC4-R
      5.2.4. COMPOUNDS THAT CAN BE SCREENED IN ACCORDANCE WITH THE INVENTION
   5.3. MC4-R PROTEINS, POLYPEPTIDES, AND ANTIBODIES
      5.3.1. PRODUCTION OF MC4-R POLYPEPTIDES
      5.3.2. ANTIBODIES TO MC4-R POLYPEPTIDES
   5.4. GENE THERAPY APPROACHES TO CONTROLLING
      5.4.1. GENE REPLACEMENT THERAPY
      5.4.2. INHIBITION OF MC4-R EXPRESSION
      5.4.3. DELIVERY OF SOLUBLE MC4-R POLYPEPTIDES
   5.5. PHARMACEUTICAL FORMULATIONS AND METHODS OF TREATING BODY WEIGHT DISORDERS
      5.5.1. DOSE DETERMINATIONS
      5.5.2. FORMULATIONS AND USE
6. EXAMPLE: GENERATION OF AN MC4-R DEFICIENT MOUSE
   6.1. MATERIALS AND METHODS
      6.1.1. IDENTIFICATION OF THE MURINE MC4-R GENE
      6.1.2. GENERATION OF THE TARGETING CONSTRUCT
      6.1.3. GENERATION OF TARGETED ES CELLS
      6.1.4. GENERATION OF MC4-R DEFICIENT MICE
      6.1.4 WEIGHT AND LENGTH MEASUREMENTS
      6.1.5. FOOD CONSUMPTION
      6.1.6. SERUM ANALYSIS
      6.1.7. HISTOLOGY
   6.2. RESULTS
      6.2.1. GENERATION OF MC4-R DEFICIENT MICE
      6.2.2. BODY WEIGHT AND SIZE OF MC4-R DEFICIENT MICE
      6.2.3. FOOD CONSUMPTION
      6.2.4. SERUM ANALYSIS
      6.2.5. POMC GENE EXPRESSION
7. EXAMPLE: AGOUTI PROTEIN BINDS DIRECTLY TO MC1-R AND MC4-R
   7.1. MATERIAL AND METHODS
   7.2. RESULTS
   7.3. DISCUSSION

1. INTRODUCTION

The present invention relates to drug screening assays, and diagnostic and therapeutic methods for the treatment of body weight disorders, such as obesity, anorexia and cachexia, involving the melanocortin 4-receptor (MC4-R). The invention also relates to compounds that modulate the activity or expression of the MC4-R, and the use of such compounds in the treatment of body weight disorders.

2. BACKGROUND OF THE INVENTION

Melanocortins (a variety of different peptide products resulting from post-translational processing of pro-opiomelanocortin) are known to have a broad array of physiological actions. Aside from their well known effects on adrenal cortical function (e.g., by ACTH, adrenocorticotropic hormone), and on melanocytes (e.g., by α-MSH, melanocyte stimulating hormone), melanocortins have been shown to affect behavior, learning, and memory, control of the cardiovascular system, analgesia, thermoregulation, and the release of other neurohumoral agents including prolactin, luteinizing hormone, and biogenic amines. Peripherally, melanocortins have been identified to have immunomodulatory and neurotrophic properties and to be involved in events surrounding parturition.

The melanocortins mediate their effects through melanocortin receptors (MC-R)—a subfamily of G-protein coupled receptors. Other than the MC1-R which was identified as specific for α-MSH, and MC2-R which was identified as specific for ACTH, the melanocortin receptors cloned and identified to date (MC3-R, MC4-R, MC5-R) are thought of as "orphan" receptors—i.e., the identity of the native ligand for each receptor remains unidentified, and the physiologic function of each receptor type remains unknown.

The agouti protein is a gene product expressed in mice that is known to be involved in determining coat color, but also thought to play a role in obesity when its normal expression pattern is de-regulated and the protein is ubiquitously expressed. The receptor for agouti has not been identified or cloned; however, it has been observed that agouti antagonizes the MSH-induced activation of two melanocortin receptors.

2.1. THE MELANOCORTIN RECEPTORS

The first two melanocortin receptors cloned were the melanocyte MSH receptor, MC1-R, and the adrenocortical ACTH receptor, MC2-R (Mountjoy et al., 1992, Science 257:1248–1251; Chhajlani & Wikberg, 1992, FEBS Lett. 309:417–420). Subsequently, three additional melanocortin receptor genes were cloned which recognize the core heptapeptide sequence (MEHFRWG) of melanocortins. Two of these receptors have been shown to be expressed primarily in the brain, MC3-R (Roselli-Rehfuss et al., 1993, Proc. Natl. Acad. Sci. USA 90:8856–8860; Gantz et al., 1993, J. Biol. Chem. 268:8246–8250) and MC4-R (Gantz et al., 1993, J. Biol. Chem. 268:15174–15179; Mountjoy et al., 1994, Mol. Endo. 8:1298–1308). A fifth melanocortin receptor (originally called MC2-R) is expressed in numerous peripheral organs as well as the brain (Chhajlani et al., 1993, Biochem. Biophys. Res. Commun. 195:866–873; Gantz et al., 1994, Biochem. Biophs. Res. Commun. 200:1214–1220). The native ligands and functions of these latter three receptors remain unknown.

Because of their "orphan" status as receptors without an identified ligand, and the absence of any known physiological role for these new receptors, investigators have attempted to characterize the receptors in vitro, by their ability to bind and respond (e.g., transduce signal) to a variety of known melanocortins (e.g., see Roselli-Rehfuss, 1993, supra; and Gantz, 1993 supra) or agonists and antagonists derived from MSH and ACTH amino acid sequences (e.g., see Hruby et al., 1995, J. Med. Chem. 38:3454–3461; and Adan et al., 1994, Eur. J. Pharmacol. 269:331–337). In another approach, the members of the melanocortin receptor family were differentiated on the basis of their pattern of tissue distribution as a means for hypothesizing a function (e.g., See Gantz, 1993, supra; and Mountjoy 1994, supra). For example, expression of MC1-R is localized to melanocytes, MC2-R is localized to adrenal cortical cells, whereas the MC3-R and MC4-R are found primarily in the brain but not in the adrenal cortex or melanocytes; MC4-R is not expressed in the placenta, a tissue that expresses large amounts of MC3-R. Based upon its expression pattern in the hippocampal region of the brain, a role for the MC4-R in learning and memory was proposed (Gantz, 1993, supra) but was noted to be a "pharmacological paradox" in that the MC4-R does not respond well to compounds known to have an effect on retention of learned behaviors. (Mountjoy, 1994, supra). Mountjoy 1994 further suggests that the MC4-R may participate in modulating the flow of visual and sensory information, or coordinate aspects of somatomotor control, and/or may participate in the modulation of autonomic outflow to the heart.

Thus, despite such efforts, the native ligands and function of MC3-R, MC4-R and MC5-R remain elusive.

2.2. THE AGOUTI PROTEIN

The agouti gene is predicted to encode a secreted protein expressed in hair follicles and the epidermis, the expression of which correlates with the synthesis of the yellow pigment associated with the agouti phenotype (Miller et al., 1993, Gene & Development 7:454–467). Certain dominant mutations of the agouti gene result in de-regulated, ubiquitous expression of the agouti protein in mice, demonstrating pleiotropic effects that include obesity and increased tumor susceptibility. (Miller et al., 1993, supra; Michaud et al., 1993, Genes & Development 7:1203–1213). Ectopic expression of the normal, wild-type, agouti protein in transgenic mice results in obesity, diabetes, and the yellow coat color commonly observed in spontaneous obese mutants (Klebig, et al., 1995, Proc. Natl. Acad. Sci. USA 92:4728–4732). For reviews, see Jackson, 1993, Nature 362:587–588; Conklin & Bourne, 1993, Nature 364:110; Siracusa 1994, TIG 10:423–428; Yen et al., 1994, FASEB J. 8:479–488; Ezzell, 1994, J. NIH Res. 6:31–33; and Manne et al., 1995, Proc. Sci. USA 92:4721–4724.

No receptor for agouti has been identified. Agouti has been reported to be a competitive antagonist of AMSH binding to the MC1-R and MC4-R in vitro (Lu et al., 1994, Nature 371:799–802), and the authors speculated that ectopic expression of agouti may lead to obesity by antagonism of melanocortin receptors expressed outside the hair follicle. In this regard, a number of theories have been proposed to account for the induction of obesity by ectopic expression of agouti. For example, agouti expression in skeletal muscle may result in insulin resistance, hyperinsulinemia and obesity via elevation of $Ca^2+$levels; alternatively ectopic agouti expression in adipocytes may depress lipolysis; conversely direct effects of agouti on pancreatic β islet cells may result in hyperinsulinemia and obesity; yet another possibility is that agouti expression in the brain may result in obesity due to a primary effect on areas of the brain controlling weight regulation and insulin production (see Klebig 1995, supra).

In sum, the mechanism of agouti-induced obesity in mice is unknown, and the relevance, if any, of this phenomenon to human obese phenotypes has not been established.

3. SUMMARY OF THE INVENTION

The present invention relates to drug screening assays to identify compounds for the treatment of body weight disorders, such as obesity, anorexia and cachexia by using MC4-R as a target. The invention also relates to compounds that modulate body weight via the MC4-R. The present invention also relates to the treatment of body weight disorders by targeting the MC4-R.

The invention is based, in part, on the discovery of a specific role for MC4-R in body weight regulation. As demonstrated herein, mice completely lacking MC4-R develop a maturity onset obesity syndrome associated with hyperphagia, hyperinsulinemia, and hyperglycemia. In particular, knock-out mice in which the gene encoding MC4-R is defective exhibit significant weight gain compared to either MC4-R heterozygous or wild-type female littermates. The invention is also based, in part, on the discovery that the agouti protein, known to be involved in an obese phenotype when ectopically expressed in mice, binds to the MC4-R.

The invention relates to assays designed to screen for compounds or compositions that modulate MC4-R activity, i.e., compounds or compositions that act as agonists or antagonists of MC4-R, and thereby modulate weight control. To this end, cell-based assays or non-cell based assays can be used to detect compounds that interact with, e.g., bind to, a MC4-R extracellular domain ("ECD"). The cell-based assays have the advantage in that they can be used to identify compounds that affect MC4-R biological activity (i.e., signal transduction), including the identification of compounds that do not interact with a MC4-R ECD, but act on an intracellular component of the signal transduction pathway mediated by MC4-R.

The invention also relates to assays designed to screen for compounds or compositions that modulate MC4-r gene expression. For example, cell-based assays, or cell-lysate assays (e.g., in vitro transcription or translation assays) can be used to screen for compounds or compositions that modulate MC4-r transcription (e.g., compounds that modulate expression, production or activity of transcription factors involved in MC4-r gene expression; polynucleotides that form triple helical structures with an MC4-r regulatory region and inhibit transcription of the MC4-r gene, etc.). Alternatively, cell-based assays or cell-lysate assays can be used to screen for compounds or compositions that modulate translation of MC4-R transcripts (e.g., antisense and ribozyme molecules).

In yet another embodiment, the cell-based assays or cell-lysate assays can be used to test polynucleotide constructs designed to modify the expression of the MC4-r gene in vivo. Such constructs include polynucleotide constructs designed for gene therapy; e.g., expression constructs or gene replacement constructs that place the MC4-r gene under the control of a strong promoter system, an inducible promoter system or a constitutive promoter system.

The invention also encompasses agonists and antagonists of MC4-R, including small molecules, large molecules, and antibodies, as well as nucleotide sequences that can be used to inhibit MC4-r gene expression (e.g., antisense and ribozyme molecules), and gene or regulatory sequence replacement constructs designed to enhance MC4-r gene expression (e.g., expression constructs that place the MC4-r gene under the control of a strong promoter system). Such compounds may be used to treat body weight disorders.

The invention also encompasses the use of such compounds and compositions, including gene therapy approaches, that modulate MC4-R activity or MC4-r gene expression to treat body weight disorders.

3.1. DEFINITIONS

The following terms as used herein shall have the meaning indicated.

MC4-r nucleotides or coding sequences: means DNA sequences encoding MC4-R mRNA transcripts, MC4-R protein, polypeptide or peptide fragments of MC4-R protein, or MC4-R fusion proteins. MC4-r nucleotide sequences encompass DNA, including genomic DNA (e.g. the MC4-r gene) or cDNA.

MC4-R means MC4-r gene products, e.g., transcripts and the MC4 receptor protein. Polypeptides or peptide fragments of the MC4-R protein are referred to as MC4-R polypeptides or MC4-R peptides. Fusions of MC4-R, or MC4-R polypeptides, or peptide fragments to an unrelated protein are referred to herein as MC4-R fusion proteins. A functional MC4-R refers to a protein which binds melanocortin peptides in vivo or in vitro.

ECD: means "extracellular domain".

TM: means "transmembrane domain".

CD: means "cytoplasmic domain".

4. DESCRIPTION OF THE FIGURES

FIGS. 1A–1B Deduced amino acid sequences of the melanocortin receptors (MC3 (SEQ ID NO: 1); MC4 (SEQ ID NO: 2); MC2 (SEQ ID NO:3); and MC1 (SEQ ID NO: 4)). The serpentine structure of the melanocortin receptors predicts that the hydrophilic domains located between the TM domains are arranged alternately outside and within the cell to form the ECD (amino acid residues 1–74, 137–155, 219–231 and 305–316 in FIGS. 1A–1B) and the CD (amino acid residues 102–112, 178–197, 251–280 and 339-end in FIGS. 1A–1B) of the receptor. The predicted transmembrane domains are denoted by overbars and Roman numerals, and the four extracellular domains (ECD1, ECD2, ECD3 and ECD4) and four cytoplasmic domains (CD1, CD2, CD3 and CD4) are indicated.

FIGS. 2A–2D. Schematic diagram of the construction of the MC4-R targeting vector. FIG. 2A. Partial restriction map of the MC4-R locus. FIG. 2B. The MC4-R KO 5' construct, containing genomic sequences from 3' of the MC4-R gene in the vector pJN2. FIG. 2C. The MC4-R KO 5'3' construct in which genomic sequences from 5' of the MC4-R gene have been inserted into the MC4 KO 5' construct. FIG. 2D. The MC4-R KO 5'3' neo construct in which a neo expression cassette has been inserted between the 5' and 3' flanking sequences of the MC4-R gene. The dotted line represents the pJN2 vector. The open box represents the PGK-neo expression cassette, the hatched box represents the MC4-R gene and the arrows indicate the direction of transcription.

FIGS. 3A–3E. Schematic diagram of the gene targeting strategy for inactivation of the MC4-R. FIG. 3A. Diagram of the MC4-R locus. The hatched box represents MC4-R coding sequences, the solid box indicates the location of the SacI-SphI probe used for identifying homologous recombinants. The arrow indicates the direction of transcription of the MC4-R gene. FIG. 3B. Diagram of the MC4-R targeting construct. The dashed line represents pJN2 plasmid sequences and the arrow indicates the direction of neo transcription. FIG. 3C. Diagram of the MC4-R locus following homologous recombination with the targeting vector. FIG. 3D. Predicted restriction fragment lengths for the wild type and mutated MC4-R loci digested with the indicated enzymes and probed with the SacI-SphI probe. FIG. 3E. Autoradiogram of a Southern blot analysis of tail DNA from F2 progeny. Genomic DNA was digested with ApaI or NcoI, as indicated and hybridized with the radiolabeled probe shown in FIG. 3A, then stripped and rehybridized with a radiolableed probe consisting of the human MC4-R coding sequence. +/+, +/−, and −/− denote DNA from wild-type, heterozygous, and homozygous F2 littermates, respectively.

Figure 4B:
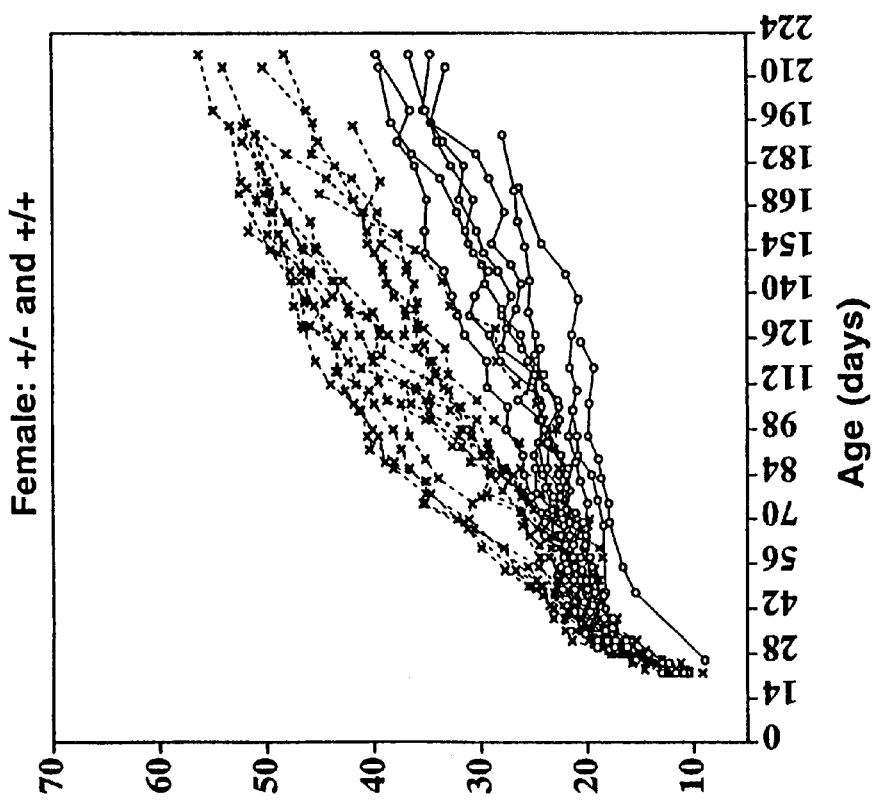
Figure 4A:
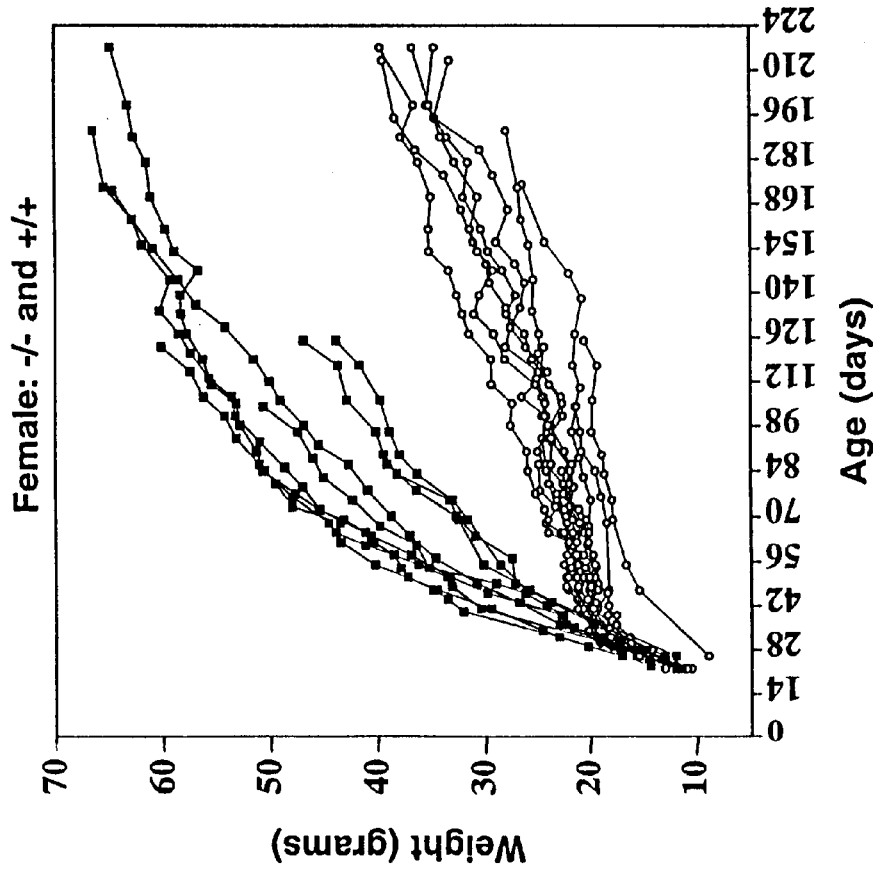
Figure 4D:
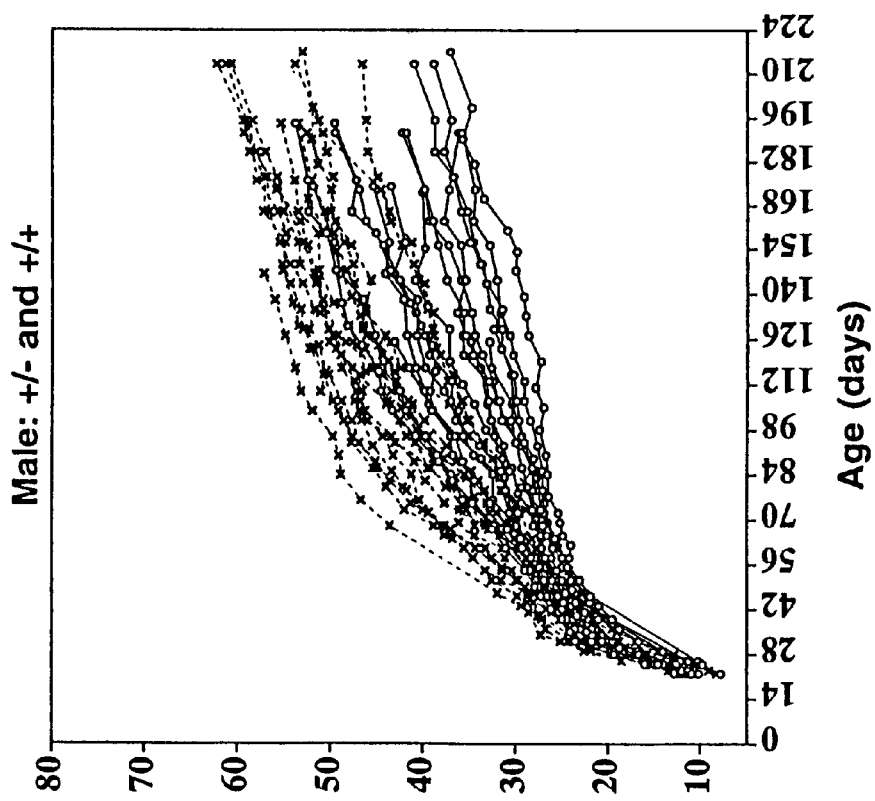
Figure 4C:
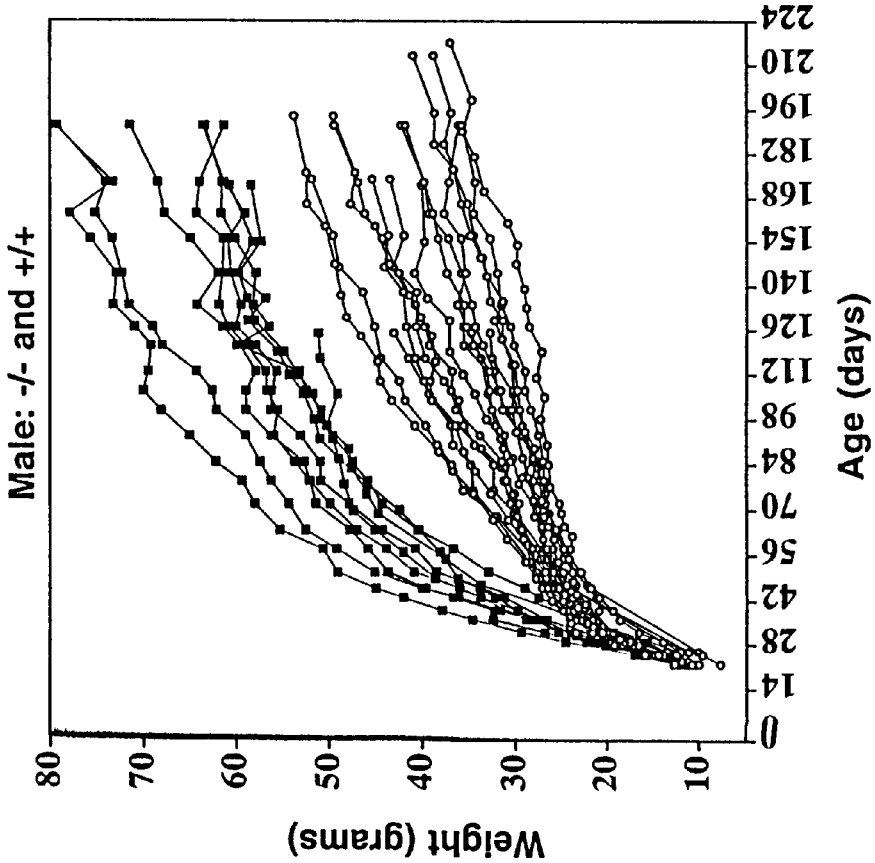

FIGS. 4A–4D. Weight gain of MC4-R deficient mice and control littermates. Each line represents the weight gain of an individual mouse. FIG. 4A. Weight gain of female homozygous (−/−) mutant mice (closed squares) and wild type (+/+) F2 controls (open circles). The weights of 9 homozygous and 12 control mice were taken at the times indicated. FIG. 4B. Weight gain of female heterozygous (+/−) mutant mice (x) and wild type (+/+) F2 controls (open circles). The weights of 18 heterozygous and 12 control mice were taken at the times indicated. FIG. 4C. Weight gain of male homozygous (−/−) mutant mice (closed squares) and wild-type (+/+) F2 controls (open circles). The weights of 9 homozygous and 17 control mice were taken at the times indicated. FIG. 4D. Weight gain of male heterozygous (+/−) mutant mice (x) and wild-type (+/+) F2 controls (open circles). The weights of 18 heterozygous and 17 control mice were taken at the times indicated.

FIGS. 5A–5C. Sequence of the human MC4-R (SEQ ID NO:5). Transmembrane domains are underlined. Amino acid differences in the rat MC4-R are indicated underneath the human sequence.

Figure 6:
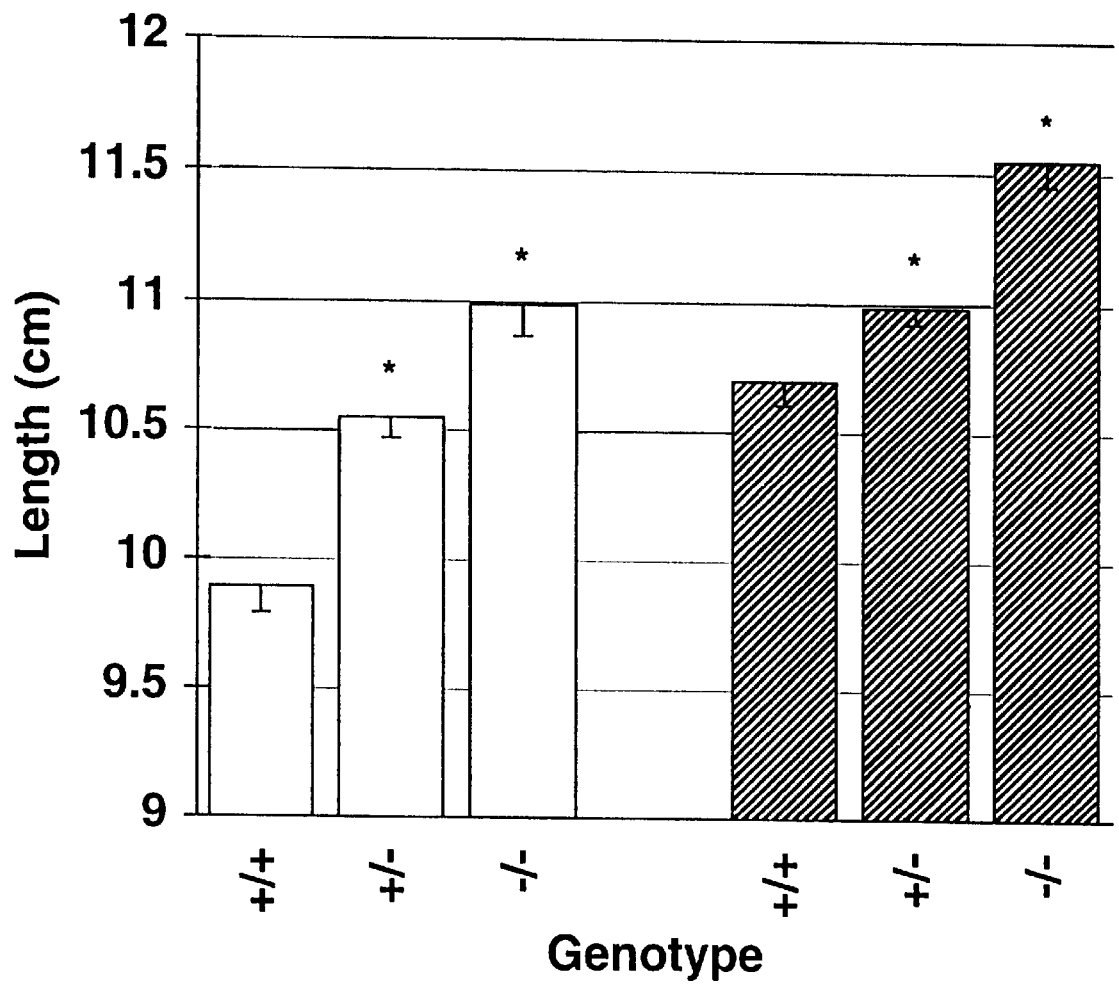

FIG. 6 Increased linear growth of MC4-R deficient mice. The body length of female (open bars) and male (cross-hatched bars) was measured at approximately 19 weeks of age (between 132–138 days). The bars indicate the mean length of 12 wild type (+/+), and 9 homozygous mutant (−/−) female F2 mice, and 15 wild type, 20 heterozygous, and 9 homozygous mutant male F2 mice. Error bars represent the standard error of the mean, and the asterisks denote significant difference (p<0.02 by two tailed Student t test) compared to the wild type value within a similar sex.

Figure 7:
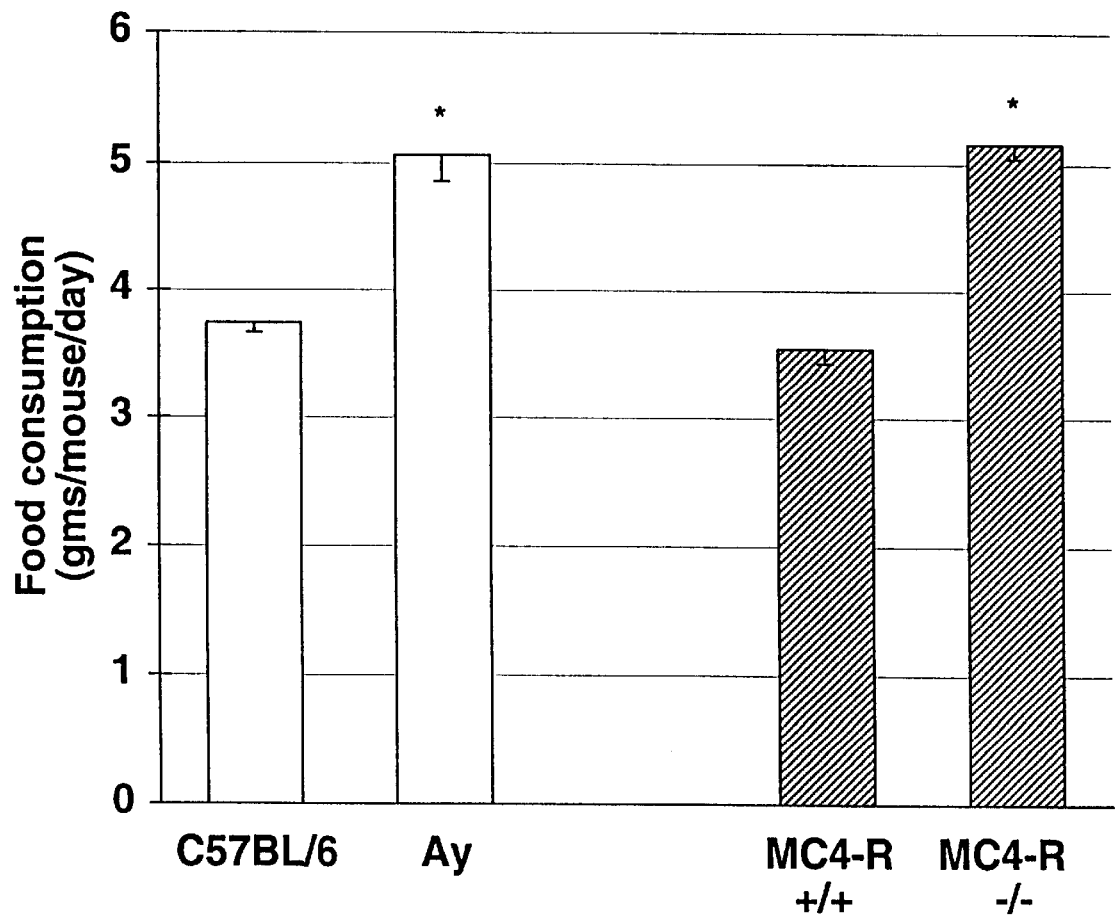

FIG. 7 Mice lacking the MC4-R are hyperphagic. The food intake of female mice housed in pairs was measured every weekday over a two week period. The open bars represent the mean of 8 measurements on one cage each of two Ay and two control C57BL/6 mice. The hatched bars represent the mean of 8 measurements on each of two cages of two homozygous mutant mice (−/−) and two F2 wild type controls (+/+). Error bars represent the standard error of the mean, and the asterisks denote significant difference (p<0.01 by two tailed Student t test) of either Ay compared to C57BL/6 or MC4-R (−/−) homozygous mutants compared to MC4-R (+/+) wild type F2 mice.

Figure 8D:
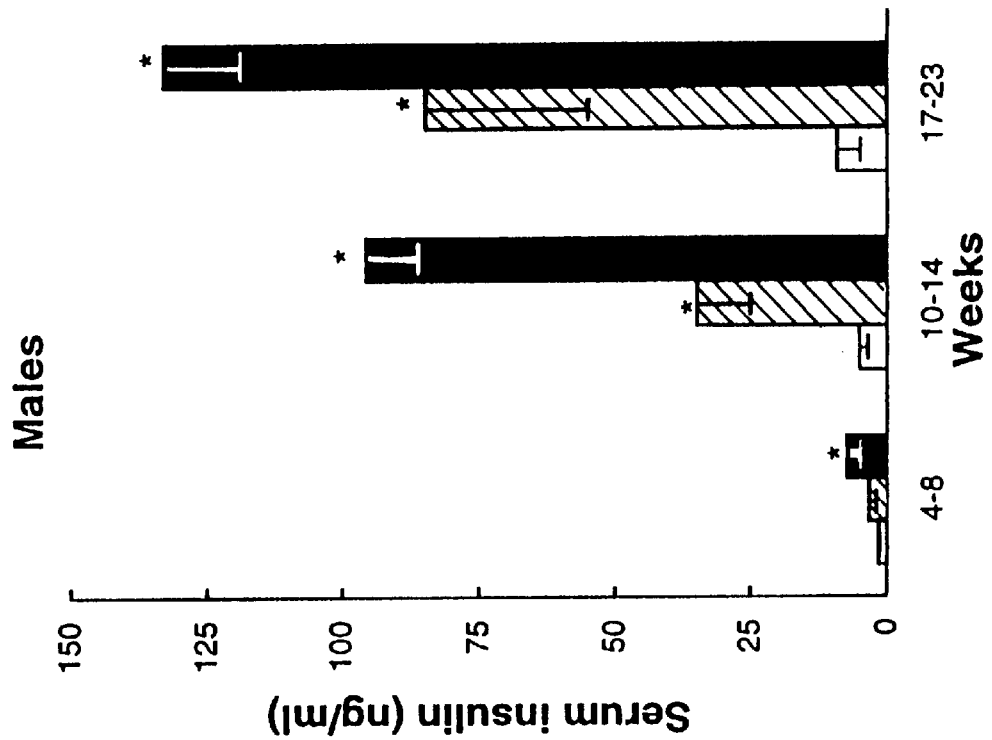
Figure 8C:
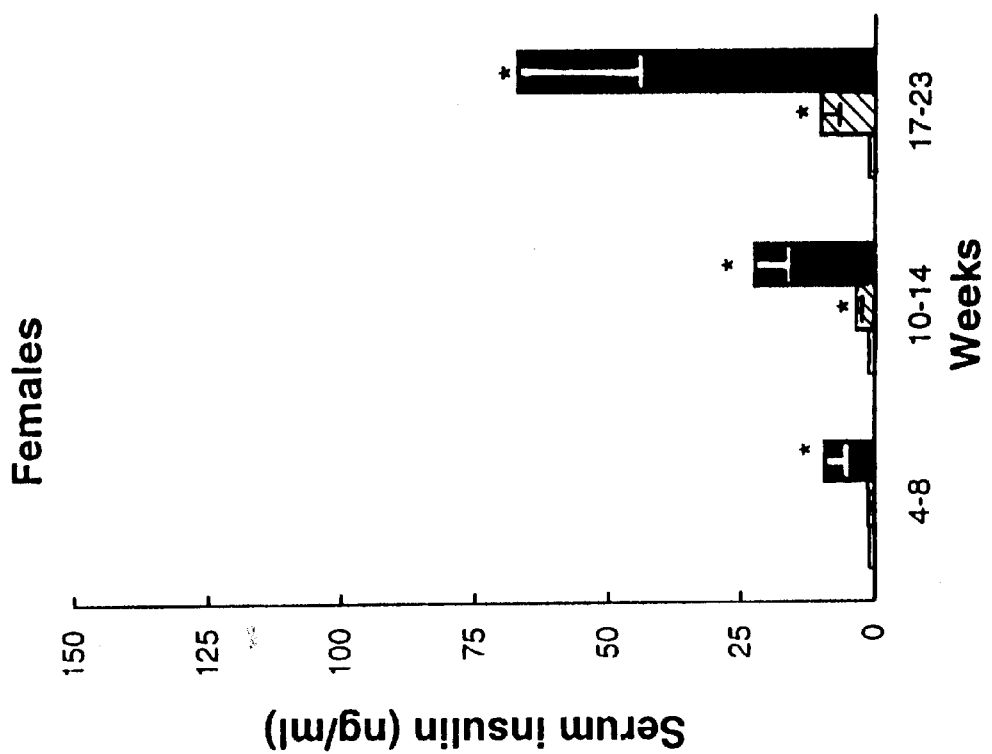

FIGS. 8A–8F. Serum glucose, insulin, and leptin levels in mice lacking the MC4-R. Glucose, insulin and leptin were each measured on the same serum samples. Open bars represent heterozygotes, and shaded bars represent homozygous mutant mice. Error bars indicate the standard error of the mean. Asterisks denote significant difference (p<0.05 by two-tailed student t test) compared to control within the same sex and age group. For female mice, the n for wild type mice at 4–8 weeks, 10–14 weeks, and 17–23 weeks was 11, 14, and 7, respectively; and for homozygous mutants, 7, 11 and 3, respectively. For male mice, the n for wild-type mice at 4–8 weeks, 10–14 weeks and 17–23 weeks was 14, 14, and 6, respectively; and for homozygous mutants, 8, 8, and 9, respectively. FIGS. 8A and 8B. Serum glucose levels of female and male mice, respectively. Five $\mu$l of serum was analyzed using a glucose oxidase assay. FIGS. 8C and 8D. Serum insulin levels of female and male mice, respectively, were assayed by radioimmunoassay using rat insulin as the standard. FIGS. 8E and 8F. Serum leptin levels of female and male mice, respectively, were measured by radioimmunoassay.

Figure 9:
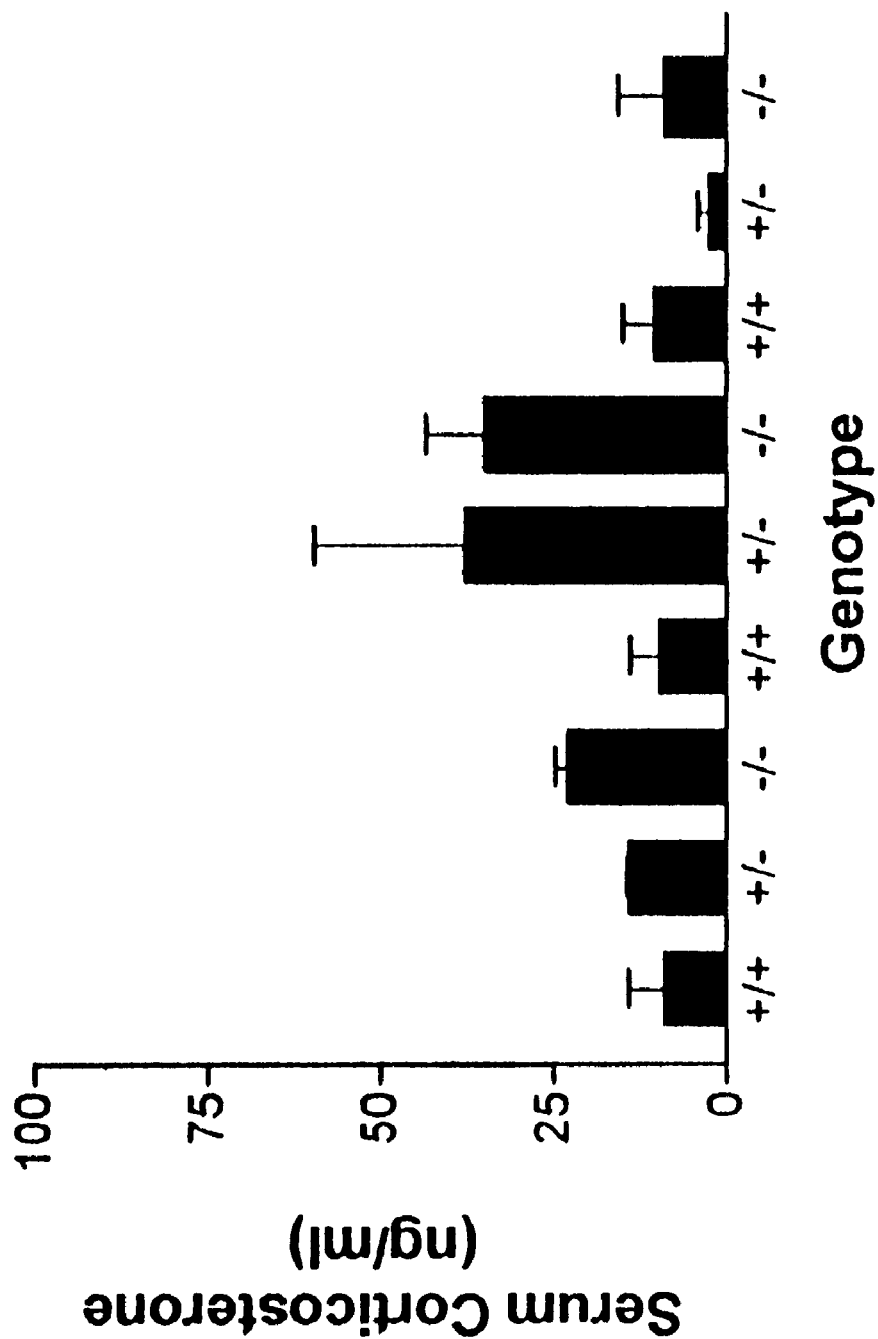

FIG. 9. MC4-R gene deletion does not affect basal serum corticosterone. Serum corticosterone levels were measured in three sets of sex matched littermates containing a representative animal of each genotype: +/+ wild-type control, +/− heterozygote, −/−homozygous mutant. Sets are, from left to right, male, female, and male. Males were 15 weeks of age, females were 18 weeks of age. Data indicate the means of measurements performed using two serum samples obtained on different days. Measurement on each day was performed in duplicate. Bars indicate standard deviation. Analysis of data by two-way ANOVA indicated no significant difference in corticosterone levels as a function of genotype.

Figure 10A:
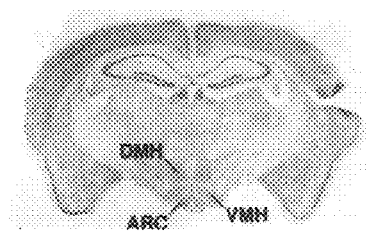
Figure 10B:
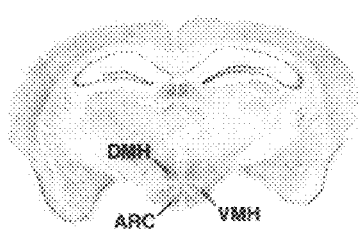
Figure 10C:
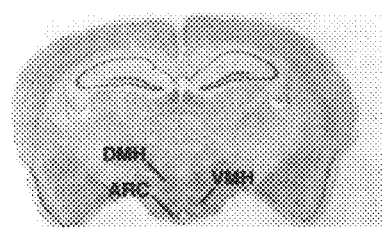
Figure 10D:
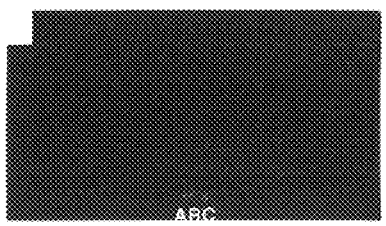
Figure 10E:
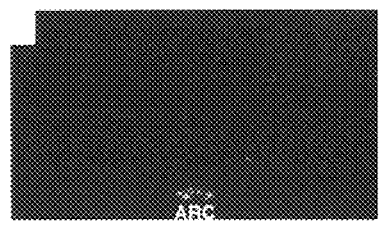
Figure 10F:
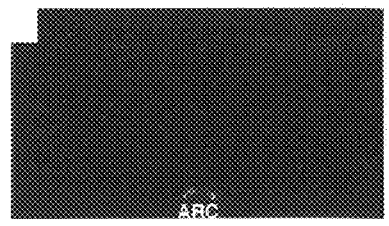

FIG. 10A–10F. MC4-R gene deletion does not effect brain POMC mRNA levels. FIGS. 10A, 10B and 10C. Hematoxylin and eosin stained brain sections from wild type, heterozygous, and homozygous mutant MC4-R deficient mice, respectively. FIGS. 10D, 10E and 10F. Autoradiographs of brain sections from wild type, heterozygous, and homozygous mutant MC4-R deficient mice, respectively, hybridized with a $^{35}$S-POMC antisense cRNA probe.

5. DETAILED DESCRIPTION OF THE INVENTION

The invention described in the subsections below encompasses screening methods (e.g., assays) for the identification of compounds which affect weight modulation. The invention also encompasses agonists and antagonists of MC4-R, including small molecules, large molecules, and antibodies, as well as nucleotide sequences that can be used to inhibit MC4-r gene expression (e.g., antisense and ribozyme molecules), and gene or regulatory sequence replacement constructs designed to enhance MC4-r gene expression (e.g., expression constructs that place the MC4-r gene under the control of a strong promoter system). Such compounds may be used to treat body weight disorders.

In particular, cellular and non-cellular assays are described that can be used to identify compounds that interact with the MC4-R, e.g., modulate the activity of the MC4-R and/or bind to the MC4-R. The cell based assays can be used to identify compounds or compositions that affect the signal-transduction activity of the MC4-R, whether they bind to the MC4-R or act on intracellular factors involved in the MC4-R signal transduction pathway. Such cell-based assays of the invention utilize cells, cell lines, or engineered cells or cell lines that express the MC4-R. The cells can be further engineered to incorporate a reporter molecule linked to the signal transduced by the activated MC4-R to aid in the identification of compounds that modulate MC4-R signalling activity.

The invention also encompasses the use of cell-based assays or cell-lysate assays (e.g., in vitro transcription or translation assays) to screen for compounds or compositions that modulate MC4-r gene expression. To this end, constructs containing a reporter sequence linked to a regulatory element of the MC4-r gene can be used in engineered cells, or in cell lysate extracts, to screen for compounds that modulate the expression of the reporter gene product at the level of transcription. For example, such assays could be used to identify compounds that modulate the expression or activity of transcription factors involved in MC4-r gene expression, or to test the activity of triple helix polynucleotides. Alternatively, engineered cells or translation extracts can be used to screen for compounds (including antisense and ribozyme constructs) that modulate the translation of MC4-R mRNA transcripts, and therefore, affect expression of the MC4-R.

The invention also encompasses MC4-R proteins, polypeptides (including soluble MC4-R polypeptides or peptides) and MC4-R fusion proteins for use in non-cell based screening assays, for use in generating antibodies, for diagnostics and therapeutics. The MC4-R is predicted to be a serpentine receptor that traverses the membrane seven times, resulting in four extra-cellular domains (ECDs) and four cellular domains (CDs) (see FIGS. 1A–1B). Peptides corresponding to each ECD, or a polypeptide composed of two or more of the four ECDs linked together can be engineered as described in Section 5.3.1, infra. Alternatively, such peptides or polypeptides can be fused to a heterologous protein, e.g., a reporter, an Ig Fc region, etc., to yield a fusion protein. Such peptides, polypeptides and fusion proteins can be used in the non-cell based assays for screening compounds that interact with, e.g., modulate the activity of the MC4-R and or bind to the MC4-R.

MC4-R protein products can be used to treat weight disorders such as obesity, anorexia or cachexia. Such MC4-R protein products include but are not limited to soluble derivatives such as peptides or polypeptides corresponding to one or more MC4-R ECDs; truncated MC4-R polypeptides lacking one or more ECD or TM; and MC4-R fusion protein products (especially MC4-R-Ig fusion proteins, i.e., fusions of the MC4-R or a domain of the MC4-R, to an IgFc domain). Alternatively, antibodies to the MC4-R or anti-idiotypic antibodies that mimic the MC4-R (including Fab fragments), antagonists or agonists (including compounds that modulate signal transduction which may act on downstream targets in the MC4-R signal transduction pathway) can be used to treat body weight disorders such as obesity, anorexia or cachexia.

For example, the administration of an effective amount of soluble MC4-R polypeptide, or an MC4-R fusion protein (e.g., MC4-R ECD-IgFc) or an anti-idiotypic antibody (or its Fab) that mimics the MC4-R ECD would interact with and thereby "mop up" or "neutralize" endogenous MC4-R ligand, and prevent or reduce binding and receptor activation, leading to weight gain. In yet another approach, nucleotide constructs encoding such MC4-R products can be used to genetically engineer host cells to express such MC4-R products in vivo; these genetically engineered cells can function as "bioreactors" in the body delivering a continuous supply of the MC4-R, MC4-R peptide, soluble MC4-R polypeptide, or MC4-R fusion protein that will "mop up" or neutralize MC4-R ligand.

"Gene therapy" approaches for the modulation of MC4-R expression and/or activity in the treatment of body weight disorders are within the scope of the invention. For example, nucleotide constructs encoding functional MC4-Rs, mutant MC4-Rs, as well as antisense and ribozyme molecules can be used to modulate MC4-r expression.

The invention also encompasses pharmaceutical formulations and methods for treating body weight disorders.

5.1. THE ROLE OF MC4-R IN THE REGULATION OF BODY WEIGHT

The specific role of the MC4-R protein in vivo was investigated by engineering MC4-R "knock out" mice in which most of the endogenous MC4-R gene coding sequence was deleted, thereby creating mice which are unable to produce functional MC4-R protein. Unlike MC-R agonist/antagonist studies which are complicated because each of the MC receptors, rather than just MC4-R, can be affected, this specific elimination of only MC4-R function allowed an evaluation of the biological function of MC4-R.

In order to produce the MC4-R knock out mice, human MC4-r gene sequences were utilized to isolate and clone the murine MC4-r gene. A murine MC4-r targeting construct was then generated which was designed to delete the majority of the murine MC4-r coding sequence upon homologous recombination with the endogenous murine MC4-r gene. Embryonic stem (ES) cells containing the disrupted MC4-r gene were produced, isolated and microinjected into murine blastocysts to yield mice chimeric for cells containing a disrupted MC4-r gene. Offspring of the chimeric mice resulting from germline transmission of the ES genome were obtained and animals heterozygous for the disrupted MC4-R were identified.

In order to assess the role of MC4-R in vivo, the animals heterozygous for the MC4-r disrupted gene were bred together, producing litters containing wild-type mice, mice heterozygous for the MC4-r mutation and mice homozygous for the MC4-R mutation. Inactivation of the MC4-R by gene targeting results in mice that develop a maturity onset obesity syndrome associated with hyperphagia, hyperinsulinemia, and hyperglycemia.

The weight gain of the animals was monitored regularly. Homozygous null MC4-R mutants showed an increase in weight compared to mice heterozygous for MC4-R deletion and wild type mice as early as 25 days of age. By approximately 5 weeks of age, most of the homozygous mutants, both males and females, were heavier than their wild type siblings of the same sex, and by 7 weeks of age all of the null mutants were heavier than the controls (FIGS. 4A and 4C). By 15 weeks of age, homozygous mutant females were on average twice as heavy as their wild-type siblings, while homozygous mutant males were approximately 50% heavier than wild-type controls. Mice heterozygous for MC4-R deletion showed a weight gain intermediate to that seen in wild-type and homozygous mutant siblings (FIGS. 4B and 4D), demonstrating a gene dosage effect of MC4-R ablation on body weight regulation.

In addition, as demonstrated in FIG. 6, MC4-R deficient mice are significantly longer than wild-type controls. The mean length of homozygous mutant females is increased approximately 11% relative to wild-type F2 mice, and heterozygous females are approximately 7% longer than controls. Male homozygotes and heterozygotes are approximately 8% and 2.5% longer than controls, respectively. Absence of the MC4-R also resulted in a significant increase (46%) in food consumption over wild-type F2 controls.

Blood was collected from MC4-R deficient mice and assayed for serum levels of glucose, insulin and leptin concentrations. Serum glucose levels were essentially unchanged in females heterozygous or homozygous for MC4-R deletion, but both heterozygous and homozygous males were hyperglycemic (FIGS. 8A and 8B). Both male and female mice were also found to be hyperinsulinemic (FIGS. 8C and 8D). Heterozygous mutants were hyperinsulinemic, although less so than homozygous mutants. In addition to glucose and insulin, serum leptin levels were altered in MC4-R deficient mice (FIGS. 8E and 8F). Heterozygous mice, for the most part, showed leptin levels intermediate between that observed for wild-type mice and homozygous mutants.

The knock out experiments described herein represent definitive evidence of the role of MC4-R in weight regulation. The experimental design does not rely on the relationship, if any, of the agouti ligand for the characterization of the functional role of the MC4-R.

5.2. SCREENING ASSAYS FOR DRUGS USEFUL IN REGULATION OF BODY WEIGHT

At least three different assay systems, described in the subsections below, can be designed and used to identify compounds or compositions that modulate MC4-R activity or MC4-r gene expression, and therefore, modulate weight control.

The systems described below may be formulated into kits. To this end, the MC4-R or cells expressing the MC4-R can be packaged in a variety of containers, e.g., vials, tubes, microtitre well plates, bottles, and the like. Other reagents can be included in separate containers and provided with the kit; e.g., positive controls samples, negative control samples, melanocortin peptides (including but not limited to αMSH and ACTH derivatives), buffers, cell culture media, etc.

5.2.1. CELL-BASED ASSAYS

In accordance with the invention, a cell-based assay system can be used to screen for compounds that modulate the activity of the MC4-R and thereby, modulate body weight. To this end, cells that endogenously express MC4-R can be used to screen for compounds. Alternatively, cell lines, such as 293 cells, COS cells, CHO cells, fibroblasts, and the like, genetically engineered to express the MC4-R can be used for screening purposes. Preferably, host cells genetically engineered to express a functional receptor that responds to activation by melanocortin peptides can be used as an endpoint in the assay; e.g., as measured by a chemical, physiological, biological, or phenotypic change, induction of a host cell gene or a reporter gene, change in cAMP levels, adenylyl cyclase activity, host cell G protein activity, extracellular acidification rate, host cell kinase activity, proliferation, differentiation, etc.

To be useful in screening assays, the host cells expressing functional MC4-R should give a significant response to MC4-R ligand, preferably greater than 5-fold induction over background. Host cells should preferably possess a number of characteristics, depending on the readout, to maximize the inductive response by melanocortin peptides, for example, for detecting a strong induction of a CRE reporter gene: (a) a low natural level of cAMP, (b) G proteins capable of interacting with the MC4-R, (c) a high level of adenylyl cyclase, (d) a high level of protein kinase A, (e) a low level of phosphodiesterases, and (f) a high level of cAMP response element binding protein would be advantageous. To increase response to melanocortin peptide, host cells could be engineered to express a greater amount of favorable factors or a lesser amount of unfavorable factors. In addition, alternative pathways for induction of the CRE reporter could be eliminated to reduce basal levels.

In utilizing such cell systems, the cells expressing the melanocortin receptor are exposed to a test compound or to vehicle controls (e.g., placebos). After exposure, the cells can be assayed to measure the expression and/or activity of components of the signal transduction pathway of the melanocortin receptor, or the activity of the signal transduction pathway itself can be assayed. For example, after exposure, cell lysates can be assayed for induction of cAMP. The ability of a test compound to increase levels of cAMP, above those levels seen with cells treated with a vehicle control, indicates that the test compound induces signal transduction mediated by the melanocortin receptor expressed by the host cell.

To determine intracellular cAMP concentrations, a scintillation proximity assay (SPA) may be utilized (SPA kit is provided by Amersham Life Sciences, Illinois). The assay utilizes $^{125}$I label cAMP, an anti-cAMP antibody, and a scintillant-incorporated microsphere coated with a secondary antibody. When brought into close proximity to the microsphere through the labeled cAMP-antibody complex, $^{125}$I will excite the scintillant to emit light. Unlabeled cAMP extracted from cells competes with the $^{125}$I-labeled cAMP for binding to the antibody and thereby diminishes scintillation. The assay may be performed in 96-well plates to enable high-throughput screening and 96 well-based scintillation counting instruments such as those manufactured by Wallac or PAckard may be used for readout.

In screening for compounds that may act as antagonists of MC4-R, it is necessary to include ligands that activate the MC4-R, e.g., α-MSH, β-MSH or ACTH, to test for inhibition of signal transduction by the test compound as compared to vehicle controls.

In a specific embodiment of the invention, constructs containing the cAMP responsive element linked to any of a variety of different reporter genes may be introduced into cells expressing the melanocortin receptor. Such reporter genes may include but is not limited to chloramphenicol acetyltransferase (CAT), luciferase, GUS, growth hormone, or placental alkaline phosphatase (SEAP). Following exposure of the cells to the test compound, the level of reporter gene expression may be quantitated to determine the test compound's ability to regulate receptor activity. Alkaline phosphatase assays are particularly useful in the practice of the invention as the enzyme is secreted from the cell. Therefore, tissue culture supernatant may be assayed for secreted alkaline phosphatase. In addition, alkaline phosphatase activity may be measured by calorimetric, bioluminescent or chemilumenscent assays such as those described in Bronstein, I. et al. (1994, Biotechniques 17: 172–177). Such assays provide a simple, sensitive easily automatable detection system for pharmaceutical screening.

When it is desired to discriminate between the melanocortin receptors and to identify compounds that selectively agonize or antagonize the MC4-R, the assays described above should be conducted using a panel of host cells, each genetically engineered to express one of the melanocortin receptors (MC1-R through MC5-R). Expression of the human melanocortin receptors is preferred for drug discovery purposes. To this end, host cells can be genetically engineered to express any of the amino acid sequences shown for melanocortin receptors 1 through 5 in FIGS. 1A–1B. The cloning and characterization of each receptor has been described: MC1-R and MC2-R (Mountjoy., 1992, Science 257: 1248–1251; Chhajlani & Wikberg, 1992 FEBS Lett. 309: 417–420); MC3-R (Roselli-Rehfuss et al., 1993, Proc. Natl. Acad. Sci., USA 90: 8856–8860; Gantz et al., 1993, J. Biol. Chem. 268: 8246–8250); MC4-R (Gantz et al., 1993, J. Biol. Chem. 268: 15174–15179; Mountjoy et al., 1994, Mol. Endo. 8: 1298–1308); and MC5-R (Chhajlani et al., 1993, Biochem. Biophys. Res. Commun. 195: 866–873; Gantz et al., 1994, Biochem. Biophys. Res. Commun. 200; 1214–1220), each of which is incorporated by reference herein in its entirety. Thus, each of the foregoing sequences can be utilized to engineer a cell or cell line that expresses one of the melanocortin receptors for use in screening assays described herein. To identify compounds that specifically or selectively regulate MC4-R activity, the activation, or inhibition of MC4-R activation is compared to the effect of the test compound on the other melanocortin receptors.

In a specific embodiment, MC1-R through MC5-R cDNAs are expressed in 293 cells under the transcriptional control of the CMV promoter. Stable cell lines are established. Because transfected human MC2-R (ACTH-R) did not express very well in 293 cells, the human adrenocortical carcinoma cell line H295 (ATCC No. CRL-2128), which expresses endogenous ACTH-R, may be used in screening assays in addition to a stable cell line that expresses transfected ACTH-R. In the first round of screening, the MC4-R expressing cell line is used to identify candidate compounds that activated the MC4-R. Once identified, those candidate compounds can be tested to determine whether they selectively activate the MC4-R. The activation of the melanocortin receptors may be assayed using, for example, the SPA assay described above.

Alternatively, if the host cells express more than one melanocortin peptide receptor, the background signal produced by these receptors in response to melanocortin peptides must be "subtracted" from the signal (see Gantz et al., supra). The background response produced by these non-MC4-R melanocortin receptors can be determined by a number of methods, including elimination of MC4-R activity by antisense, antibody or antagonist. In this regard, it should be noted that wild type CHO cells demonstrate a small endogenous response to melanocortin peptides which must be subtracted from background. Alternatively, activity contributed from other melanocortin receptors could be eliminated by activating host cells with a MC4-R-specific ligand, or including specific inhibitors of the other melanocortin receptors.

5.2.2. NON-CELL BASED ASSAYS

In addition to cell based assays, non-cell based assay systems may be used to identify compounds that interact with, e.g., bind to MC4-R. Such compounds may act as antagonists or agonists of MC4-R activity and may be used in the treatment of body weight disorders.

Isolated membranes may be used to identify compounds that interact with MC4-R. For example, in a typical experiment using isolated membranes, 293 cells may be genetically engineered to express the MC4-R. Membranes can be harvested by standard techniques and used in an in vitro binding assay. $^{125}$I-labelled ligand (e.g., $^{125}$I-labelled α-MSH, β-MSH, or ACTH) is bound to the membranes and assayed for specific activity; specific binding is determined by comparison with binding assays performed in the presence of excess unlabelled ligand.

To identify MC4-R ligands, membranes are incubated with labelled ligand in the presence or absence of test compound. Compounds that bind to the receptor and compete with labelled ligand for binding to the membranes reduced the signal compared to the vehicle control samples.

Alternatively, soluble MC4-R may be recombinantly expressed and utilized in non-cell based assays to identify compounds that bind to MC4-R. The recombinantly expressed MC4-R polypeptides or fusion proteins containing one or more of the ECDs of MC4-R prepared as described in Section 5.3.1, infra, can be used in the non-cell based screening assays. Alternatively, peptides corresponding to one or more of the CDs of MC4-R, or fusion proteins containing one or more of the CDs of MC4-R can be used in non-cell based assay systems to identify compounds that bind to the cytoplasmic portion of the MC4-R; such compounds may be useful to modulate the signal transduction pathway of the MC4-R. In non-cell based assays the recombinantly expressed MC4-R is attached to a solid substrate such as a test tube, microtitre well or a column, by means well known to those in the art (see Ausubel et al., supra). The test compounds are then assayed for their ability to bind to the MC4-R.

In one aspect of the invention the screens may be designed to identify compounds that antagonize the interaction between MC4-R and MC4-R ligands such as α-MSH, β-MSH and ACTH. In such screens, the MC4-R ligands are labelled and test compounds can be assayed for their ability to antagonize the binding of labelled ligand to MC4-R.

5.2.3. ASSAYS FOR COMPOUNDS OR COMPOSITIONS THAT MODULATE EXPRESSION OF THE MC4-R

In vitro cell based assays may be designed to screen for compounds that regulate MC4-R expression at either the transcriptional or translational level.

In one embodiment, DNA encoding a reporter molecule can be linked to a regulatory element of the MC4-r gene and used in appropriate intact cells, cell extracts or lysates to identify compounds that modulate MC4-r gene expression. Appropriate cells or cell extracts are prepared from any cell type that normally expresses the MC4-r gene, thereby ensuring that the cell extracts contain the transcription factors required for in vitro or in vivo transcription. The screen can be used to identify compounds that modulate the expression of the reporter construct. In such screens, the level of reporter gene expression is determined in the presence of the test compound and compared to the level of expression in the absence of the test compound.

To identify compounds that regulate MC4-R translation, cells or in vitro cell lysates containing MC4-R transcripts may be tested for modulation of MC4-R mRNA translation. To assay for inhibitors of MC4-R translation, test compounds are assayed for their ability to modulate the translation of MC4-R mRNA in in vitro translation extracts.

Compounds that decrease the level of MC4-R expression, either at the transcriptional or translational level, may be useful for treatment of body weight disorders such as anorexia and cachexia. In contrast, those compounds that increase the expression of MC4-R may be useful for treatment of disorders such as obesity.

5.2.4. COMPOUNDS THAT CAN BE SCREENED IN ACCORDANCE WITH THE INVENTION

The assays described above can identify compounds which affect MC4-R activity. For example, compounds that affect MC4-R activity include but are not limited to compounds that bind to the MC4-R, inhibit binding of the natural ligand, and either activate signal transduction (agonists) or block activation (antagonists), and compounds that bind to the natural ligand of the MC4-R and neutralize ligand activity. Compounds that affect MC4-r gene activity (by affecting MC4-r gene expression, including molecules, e.g., proteins or small organic molecules, that affect transcription or interfere with splicing events so that expression of the full length or the truncated form of the MC4-R can be modulated) can also be identified on the screens of the invention. However, it should be noted that the assays described can also identify compounds that modulate MC4-R signal transduction (e.g., compounds which affect downstream signalling events, such as inhibitors or enhancers of G protein activities which participate in transducing the signal activated by ligand binding to the MC4-R). The identification and use of such compounds which affect signalling events downstream of MC4-R and thus modulate effects of MC4-R on the development of body weight disorders are within the scope of the invention. In some instances, G protein-coupled receptors response has been observed to subside, or become desensitized with prolonged exposure to ligand. In an embodiment of the invention assays may be utilized to identify compounds that block the desensitization of the MC4-receptor, such compounds may be used to sustain the activity of the MC4-receptor, such compounds may be used to sustain the activity of the MC4-R receptor. Such compounds can be used as part of a therapeutic method for the treatment of body weight disorders.

The compounds which may be screened in accordance with the invention include, but are not limited to peptides, antibodies and fragments thereof, and other organic compounds (e.g., peptidomimetics) that bind to the ECD of the MC4-R and either mimic the activity triggered by the natural ligand (i.e., agonists) or inhibit the activity triggered by the natural ligand (i.e., antagonists); as well as peptides, antibodies or fragments thereof, and other organic compounds that include the ECD of the MC4-R (or a portion thereof) and bind to and "neutralize" natural ligand.

Compounds may include, but are not limited to, peptides such as, for example, soluble peptides, including but not limited to members of random peptide libraries; (see, e.g., Lam, K. S. et al., 1991, Nature 354:82–84; Houghten, R. et al., 1991, Nature 354:84–86), and combinatorial chemistry-derived molecular library made of D- and/or L-configuration amino acids, phosphopeptides (including, but not limited to, members of random or partially degenerate, directed phosphopeptide libraries; see, e.g., Songyang, Z. et al., 1993, Cell 72:767–778), antibodies (including, but not limited to, polyclonal, monoclonal, humanized, anti-idiotypic, chimeric or single chain antibodies, and FAb, F(ab')$_2$ and FAb expression library fragments, and epitope-binding fragments thereof), and small organic or inorganic molecules.

Other compounds which can be screened in accordance with the invention include but are not limited to small organic molecules that are able to cross the blood-brain barrier, gain entry into an appropriate cell and affect the expression of the MC4-R gene or some other gene involved in the MC4-R signal transduction pathway (e.g., by interacting with the regulatory region or transcription factors involved in gene expression); or such compounds that affect the activity of the MC4-R or the activity of some other intracellular factor involved in the MC4-R signal transduction pathway, such as, for example, the MC4-R associated G protein.

Computer modelling and searching technologies permit identification of compounds, or the improvement of already identified compounds, that can modulate MC4-R expression or activity. Having identified such a compound or composition, the active sites or regions are identified. Such active sites might typically be ligand binding sites. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found.

Next, the three dimensional geometric structure of the active site is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures. The geometric structures may be measured with a complexed ligand, natural or artificial, which may increase the accuracy of the active site structure determined.

If an incomplete or insufficiently accurate structure is determined, the methods of computer based numerical modelling can be used to complete the structure or improve its accuracy. Any recognized modelling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential MC4-R modulating compounds.

Alternatively, these methods can be used to identify improved modulating compounds from an already known modulating compound or ligand. The composition of the known compound can be modified and the structural effects of modification can be determined using the experimental and computer modelling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Further experimental and computer modeling methods useful to identify modulating compounds based upon identification of the active sites of MC4-R, and related transduction and transcription factors will be apparent to those of skill in the art.

Examples of molecular modelling systems are the CHARMm and QUANTA programs (Polygen Corporation, Waltham, Mass.). CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modelling of drugs interactive with specific proteins, such as Rotivinen, et al.) 1988, Acta Pharmaceutical Fennica 97:159–166); Ripka (1988 New Scientist 54–57); McKinaly and Rossmann (1989, Annu. Rev. Pharmacol. Toxiciol. 29:111–122); Perry and Davies, OSAR: Quantitative Structure-Activity Relationships in Drug Design pp. 189–193 Alan R. Liss, Inc. 1989; Lewis and Dean (1989, Proc. R. Soc. Lond. 236:125–140 and 141–162); and, with respect to a model receptor for nucleic acid components, Askew, et al. (1989, J. Am. Chem. Soc. 111:1082–1090). Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to regions of DNA or RNA, once that region is identified.

Although described above with reference to design and generation of compounds which could alter binding, one could also screen libraries of known compounds, including natural products or synthetic chemicals, and biologically active materials, including proteins, for compounds which are inhibitors or activators.

Compounds identified via assays such as those described herein may be useful, for example, in elaborating the biological function of the MC4-R gene product, and for ameliorating body weight disorders. Assays for testing the efficacy of compounds identified in the cellular screen can be tested in animal model systems for body weight disorders. Such animal models may be used as test substrates for the identification of drugs, pharmaceuticals, therapies and interventions which may be effective in treating such disorders. For example, animal models may be exposed to a compound, suspected of exhibiting an ability to ameliorate body weight disorder symptoms, at a sufficient concentration and for a time sufficient to elicit such an amelioration of body weight: disorder symptoms in the exposed animals. The response of the animals to the exposure may be monitored by assessing the reversal of disorders associated with body weight disorders such as obesity. With regard to intervention, any treatments which reverse any aspect of body weight disorder-like symptoms should be considered as candidates for human body weight disorder therapeutic intervention. Dosages of test agents may be determined by deriving dose-response curves, as discussed in Section 5.5, below.

To this end, transgenic animals that express the human MC4-r gene products can be used. Animals of any species, including, but not limited to, mice, rats, rabbits, guinea pigs, pigs, micro-pigs, goats, and non-human primates, e.g., baboons, monkeys, and chimpanzees may be used to generate MC4-R transgenic animals.

Any technique known in the art may be used to introduce the human MC4-r transgene into animals to produce the founder lines of transgenic animals. Such techniques include, but are not limited to pronuclear microinjection (Hoppe, P. C. and Wagner, 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the MC4-r transgene in all their cells, as well as animals which carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, M. et al., 1992, Proc. Natl. Acad. Sci. USA 89: 6232–6236). The regulatory sequences required for such a cell-type specific activation will depend upon the particular cell type of interest, and will be apparent to those of skill in the art. When it is desired that the MC4-r transgene be integrated into the chromosomal site of the endogenous MC4-r gene, gene targeting is preferred. Briefly, when such a technique is to be utilized, vectors containing nucleotide sequences homologous to the endogenous MC4-r gene and/ or sequences flanking the gene are designed for the purpose of integrating, via homologous recombination with chromosomal sequences, into and disrupting the function of the endogenous MC4-r gene. The transgene may also be selectively expressed in a particular cell type with concomitant inactivation of the endogenous MC4-r gene in only that cell type, by following, for example, the teaching of Gu et al. (Gu, et al., 1994, Science 265: 103–106). The regulatory sequences required for such a cell-type specific recombination will depend upon the particular cell type of interest, and will be apparent to those of skill in the art.

Once founder animals have been generated, standard techniques such as Southern blot analysis or PCR techniques are used to analyze animal tissues to determine whether integration of the transgene has taken place. The level of mRNA expression of the transgene in the tissues of the founder animals may also be assessed using techniques which include but are not limited to Northern blot analysis of tissue samples obtained from the animal, in situ hybridization analysis, and RT-PCR. Samples of MC4-R gene-expressing tissue, may also be evaluated immunocytochemically using antibodies specific for the MC4-R transgene product.

5.3. MC4-R PROTEINS, POLYPEPTIDES, AND ANTIBODIES

MC4-R protein, polypeptides and peptide fragments, mutated, truncated or deleted forms of the MC4-R and/or MC4-R fusion proteins can be prepared for a variety of uses, including but not limited to the generation of antibodies, as reagents in diagnostic assays, the identification of other cellular gene products involved in the regulation of body weight, as reagents in assays for screening for compounds that can be used in the treatment of body weight disorders, and as pharmaceutical reagents useful in the treatment of body weight disorders related to the MC4-R.

5.3.1. PRODUCTION OF MC4-R POLYPEPTIDES

The deduced amino acid sequences of the melanocortin receptors, including MC4-R, are shown in FIGS. 1A–1B (MC3 (SEQ ID NO: 1); MC4 (SEQ ID NO: 2); MC2 (SEQ ID NO: 3); and MC1 (SEQ ID NO: 4)), where predicted transmembrane domains are denoted by overbars and Roman numerals, and the four extracellular domains (ECD1, ECD2, ECD3, and ECD4) and the four cytoplasmic domains (CD1, CD2, CD3 and CD4) are indicated. The serpentine structure of the melanocortin receptors predicts that the hydrophilic domains located between the TM domains are arranged alternately outside and within the cell to form the ECD (amino acid residues 1–74, 137–155, 219–231 and 305–316 in FIGS. 1A–1B) and the CD (amino acid residues 102–112, 178–197, 251–280 and 339—end in FIGS. 1A–1B) of the receptor. Peptides corresponding to one or more domains of the MC4-R (e.g., ECDs, TMs or CDs), truncated or deleted MC4-R (e.g., MC4-R in which one or more of the ECDs, TMs and/or CDs is deleted) as well as fusion proteins in which the full length MC4-R, an MC4-R peptide or truncated MC4-R is fused to an unrelated protein are also within the scope of the invention. Such soluble peptides, proteins, fusion proteins, or antibodies (including anti-idiotypic antibodies) that bind to and "neutralize" circulating natural ligand for the MC4-R, can be used as described in Section 5,5, infra, to effectuate weight gain. To this end, peptides corresponding to individual ECDs of MC4-R, soluble deletion mutants of MC4-R (e.g., ΔTM mutants), or the entire MC4-R ECD (engineered by linking the four ECDs together as described below) can be fused to another polypeptide (e.g., an IgFc polypeptide). Fusion of the MC4-R or the MC4-R ECD to an IgFc polypeptide should not only increase the stability of the preparation, but will increase the half-life and activity of the MC4-R-Ig fusion protein in vivo. The Fc region of the Ig portion of the fusion protein may be further modified to reduce immunoglobulin effector function.

Such peptides, polypeptides, and fusion proteins can be prepared by recombinant DNA techniques. For example, nucleotide sequences encoding one or more of the four domains of the ECD of the serpentine MC4-R can be synthesized or cloned and ligated together to encode a soluble ECD of the MC4-R. The DNA sequence encoding one or more of the four ECDs (ECD1–4 in FIGS. 1A–1B (MC3 (SEQ ID NO: 1); MC4 (SEQ ID NO: 2); MC2 (SEQ ID NO:3); and MC1 (SEQ ID NO: 4)) can be ligated together directly or via a linker oligonucleotide that encodes a peptide spacer. Such linkers may encode flexible, glycine-rich amino acid sequences thereby allowing the domains that are strung together to assume a conformation that can bind MC4-R ligands. Alternatively, nucleotide sequences encoding individual domains within the ECD can be used to express MC4-R peptides.

A variety of host-expression vector systems may be utilized to express nucleotide sequences encoding the appropriate regions of the MC4-R to produce such polypeptides. Where the resulting peptide or polypeptide is a soluble derivative (e.g., peptides corresponding to the ECDs; truncated or deleted in which the TMs and/or CDs are deleted) the peptide or polypeptide can be recovered from the culture media. Where the polypeptide or protein is not secreted, the MC4-R product can be recovered from the host cell itself.

The host-expression vector systems also encompass engineered host cells that express the MC4-R or functional equivalents in situ, i.e., anchored in the cell membrane. Purification or enrichment of the MC4-R from such expression systems can be accomplished using appropriate detergents and lipid micelles and methods well known to those skilled in the art. However, such engineered host cells themselves may be used in situations where it is important not only to retain the structural and functional characteristics of the MC4-R, but to assess biological activity, e.g., in drug screening assays.

The host-expression vector systems that may be used for purposes of the invention include but are not limited to microorganisms such as bacteria (e.g., *E. coli, B. subtilis*) transformed with recombinant bacteriophage DNA, plasmid DNA or cosmid DNA expression vectors containing Mc4-R nucleotide sequences; yeast (e.g., Saccharomyces, Pichia) transformed with recombinant yeast expression vectors containing the MC4-R nucleotide sequences; insect cell systems infected with recombinant virus expression vectors (e.g., baculovirus) containing the MC4-R sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing MC4-R nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the MC4-R gene product being expressed. For example, when a large quantity of such a protein is to be produced, for the generation of pharmaceutical compositions of MC4-R protein or for raising antibodies to the MC4-R protein, for example, vectors which direct the expression of high levels of fusion protein products that are readily purified may be desirable. Such vectors include, but are not limited, to the *E. coli* expression vector pUR278 (Ruther et al., 1983, EMBO J. 2:1791), in which the MC4-R coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88: 8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers.

In an insect system, *Autographa californica* nuclear polyhedrosis virus (AcNPV) is used as a vector to express foreign genes. The virus grows in *Spodoptera frugiperda* cells. The MC4-R coding sequence may be cloned individually into non-essential regions (for example the polyhedrin gene) of the virus and placed under control of an AcNPV promoter (for example the polyhedrin promoter). Successful insertion of MC4-R gene coding sequence will result in inactivation of the polyhedrin gene and production of non-occluded recombinant virus (i.e., virus lacking the proteinaceous coat coded for by the polyhedrin gene). The recombinant viruses are then used to infect cells in which the inserted gene is expressed. (E.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the MC4-R nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the MC4-R gene product in infected hosts. (E.g., See Logan & Shenk, 1984, Proc. Natl. Acad. Sci. USA 81:3655–3659). Specific initiation signals may also be required for efficient translation of inserted MC4-R nucleotide sequences. These signals include the ATG initiation codon and adjacent sequences. In cases where an entire MC4-R gene or cDNA, including its own initiation codon and adjacent sequences, is inserted into the appropriate expression vector, no additional translational control signals may be needed. However, in cases where only a portion of the MC4-R coding sequence is inserted, exogenous translational control signals, including, perhaps, the ATG initiation codon, must be provided. Furthermore, the initiation codon must be in frame with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bittner et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. Accordingly, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3 and WI38 cell lines.

For long-term, high-yield production of recombinant proteins, stable expression is preferred. For example, cell lines which stably express the MC4-R sequences described above may be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the MC4-R gene product. Such engineered cell lines may be particularly useful in screening and evaluation of compounds that affect the endogenous activity of the MC4-R gene product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in $tk^-$, $hgprt^-$ or $aprt^-$ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

5.3.2. ANTIBODIES TO MC4-R POLYPEPTIDES

Antibodies that specifically recognize one or more epitopes of MC4-R, or epitopes of conserved variants of MC4-R, or peptide fragments of the MC4-R are also encompassed by the invention. Such antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

The antibodies of the invention may be used, for example, in the detection of the MC4-R in a biological sample and may, therefore, be utilized as part of a diagnostic or prognostic technique whereby patients may be tested for abnormal amounts of MC4-R. Such antibodies may also be utilized in conjunction with, for example, compound screening schemes, as described, above, for the evaluation of the effect of test compounds on expression and/or activity of the MC4-R gene product. Additionally, such antibodies can be used in conjunction with the gene therapy techniques described, below, e.g., to evaluate the normal and/or engineered MC4-R-expressing cells prior to their introduction into the patient. Such antibodies may additionally be used as a method for the inhibition of abnormal MC4-R activity. Thus, such antibodies may, therefore, be utilized as part of weight disorder treatment methods.

For the production of antibodies, various host animals may be immunized by injection with the MC4-R, an MC4-R peptide (e.g., one corresponding the a functional domain of the receptor, such as ECD, TM or CD), truncated MC4-R polypeptides (MC4-R in which one or more domains, e.g., the TM or CD, has been deleted), functional equivalents of the MC4-R or mutants of the MC4-R. Such host animals may include but are not limited to rabbits, mice, hamsters and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Polyclonal antibodies are heterogeneous populations of antibody molecules derived from the sera of the immunized animals.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against MC4-R gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

Antibodies to the MC4-R can, in turn, be utilized to generate anti-idiotype antibodies that "mimic" the MC4-R, using techniques well known to those skilled in the art. (See, e.g., Greenspan & Bona, 1993, FASEB J 7(5):437–444; and Nissinoff, 1991, J. Immunol. 147(8):2429–2438). For example antibodies which bind to the MC4-R ECD and competitively inhibit the binding of melanocortins to the MC4-R can be used to generate anti-idiotypes that "mimic" the ECD and, therefore, bind and neutralize melanocortins. Such neutralizing anti-idiotypes or Fab fragments of such anti-idiotypes can be used in therapeutic regimens to neutralize the native ligand and promote weight gain.

Alternatively, antibodies to MC4-R that can act as agonists of MC4-R activity can be generated. Such antibodies will bind to the MC4-R and activate the signal transducing activity of the receptor. Such antibodies would be particularly useful for treating weight disorders such as obesity. In addition, antibodies that act as antagonist of MC4-R activity, i.e. inhibit the activation of MC4-R receptor may be used to treat weight disorders such as anorexia or cachexia.

5.4. GENE THERAPY APPROACHES TO CONTROLLING MC4-R ACTIVITY AND REGULATING BODY WEIGHT

The expression of MC4-R can be controlled in vivo (e.g. at the transcriptional or translational level) using gene therapy approaches to regulate MC4-R activity and treat body weight disorders. Certain approaches are described below.

5.4.1. GENE REPLACEMENT THERAPY

With respect to an increase in the level of normal MC4-R gene expression and/or MC4-R gene product activity, MC4-R nucleic acid sequences can be utilized for the treatment of body weight disorders, including obesity. Where the cause of obesity is a defective MC4-R gene, treatment can be administered, for example, in the form of gene replacement therapy. Specifically, one or more copies of a normal MC4-R gene or a portion of the MC4-R gene that directs the production of an MC4-R gene product exhibiting normal function, may be inserted into the appropriate cells within a patient or animal subject, using vectors which include, but are not limited to adenovirus, adeno-associated virus, retrovirus and herpes virus vectors, in addition to other particles that introduce DNA into cells, such as liposomes.

Because the MC4-R gene is expressed in the brain, including the cortex, thalamus, brain stem and spinal cord and hypothalamus, such gene replacement therapy techniques should be capable of delivering MC4-R gene sequences to these cell types within patients. Thus, the techniques for delivery of the MC4-R gene sequences should be designed to readily cross the blood-brain barrier, which are well known to those of skill in the art (see, e.g., PCT application, publication No. WO89/10134, which is incorporated herein by reference in its entirety), or, alternatively, should involve direct administration of such MC4-R gene sequences to the site of the cells in which the MC4-R gene sequences are to be expressed.

Alternatively, targeted homologous recombination can be utilized to correct the defective endogenous MC4-R gene in the appropriate tissue; e.g., brain tissue. In animals, targeted homologous recombination can be used to correct the defect in ES cells in order to generate offspring with a corrected trait.

Additional methods which may be utilized to increase the overall level of MC4-R gene expression and/or MC4-R activity include the introduction of appropriate MC4-R-expressing cells, preferably autologous cells, into a patient at positions and in numbers which are sufficient to ameliorate the symptoms of body weight disorders, including obesity. Such cells may be either recombinant or non-recombinant. Among the cells which can be administered to increase the overall level of MC4-R gene expression in a patient are normal cells, or hypothalamus cells which express the MC4-R gene. The cells can be administered at the anatomical site in the brain, or as part of a tissue graft located at a different site in the body. Such cell-based gene therapy techniques are well known to those skilled in the art, see, e.g., Anderson, et al., U.S. Pat. No. 5,399,349; Mulligan & Wilson, U.S. Pat. No. 5,460,959.

Finally, compounds, identified in the assays described above, that stimulate or enhance the signal transduced by activated MC4-R, e.g., by activating downstream signalling proteins in the MC4-R cascade and thereby by-passing the defective MC4-R, can be used to achieve weight loss. The formulation and mode of administration will depend upon the physico-chemical properties of the compound. The administration should include known techniques that allow for a crossing of the blood-brain barrier.

5.4.2. INHIBITION OF MC4-R EXPRESSION

In an alternate embodiment, weight gain therapy can be designed to reduce the level of endogenous MC4-R gene expression, e.g., using antisense or ribozyme approaches to inhibit or prevent translation of MC4-R mRNA transcripts; triple helix approaches to inhibit transcription of the MC4-R gene; or targeted homologous recombination to inactivate or "knock out" the MC4-R gene or its endogenous promoter. Such gene therapy may be utilized for treatment of body weight disorders such as cachexia and anorexia where the inhibition of MC4-R expression is designed to increase body weight. Because the MC4-R gene is expressed in the brain, delivery techniques should be preferably designed to cross the blood-brain barrier (see PCT WO89/10134, which is incorporated by reference herein in its entirety). Alternatively, the antisense, ribozyme or DNA constructs described herein could be administered directly to the site containing the target cells.

Antisense approaches involve the design of oligonucleotides (either DNA or RNA) that are complementary to mRNA. The antisense oligonucleotides will bind to the complementary mRNA transcripts and prevent translation. Absolute complementarily, although preferred, is not required. A sequence "complementary" to a portion of an RNA, as referred to herein, means a sequence having sufficient complementarily to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarily and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

While antisense nucleotides complementary to the coding region sequence could be used, those complementary to the transcribed untranslated region are most preferred. Oligonucleotides that are complementary to the 5' end of the message, e.g., the 5' untranslated sequence up to and including the AUG initiation codon, should work most efficiently at inhibiting translation (see FIGS. 5A–5C). However, sequences complementary to the 3' untranslated sequences of mRNAs have recently shown to be effective at inhibiting translation of mRNAs as well. See generally, Wagner, R., 1994, Nature 372:333–335. Thus, oligonucleotides complementary to either the 5'- or 3'- non-translated, non-coding regions of MC4-R could be used in an antisense approach to inhibit translation of endogenous mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of MC4-R mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, a hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

The antisense molecules should be delivered to cells which express the MC4-R in vivo, e.g., neural tissue. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous MC4-R transcripts and thereby prevent translation of the MC4-R mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), etc. Any type of plasmid, cosmid, YAC or viral vector can be used to prepare the recombinant DNA construct which can be introduced directly into the tissue site; e.g., the choroid plexus or hypothalamus. Alternatively, viral vectors can be used which selectively infect the desired tissue; (e.g., for brain, herpesvirus vectors may be used), in which case administration may be accomplished by another route (e.g., systemically).

Ribozyme molecules designed to catalytically cleave MC4-R mRNA transcripts can also be used to prevent translation of MC4-R MRNA and expression of MC4-R. (See, e.g., PCT International Publication WO90/11364, published Oct. 4, 1990; Sarver et al., 1990, Science 247:1222–1225). While ribozymes that cleave mRNA at site specific recognition sequences can be used to destroy MC4-R mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585–591. There are hundreds of potential hammerhead ribozyme cleavage sites within the nucleotide sequence of human MC4-R cDNA (see FIGS. 5A–5C (SEQ ID NO: 5). Preferably the ribozyme is engineered so that the cleavage recognition site is located near the 5' end of the MC4-R mRNA; i.e., to increase efficiency and minimize the intracellular accumulation of non-functional mRNA transcripts.

The ribozymes of the present invention also include RNA endoribonucleases (hereinafter "Cech-type ribozymes") such as the one which occurs naturally in Tetrahymena Thermophila (known as the IVS, or L-19 IVS RNA) and which has been extensively described by Thomas Cech and collaborators (Zaug, et al., 1984, Science, 224:574–578; Zaug and Cech, 1986, Science, 231:470–475; Zaug, et al., 1986, Nature, 324:429–433; published International patent application No. WO88/04300 by University Patents Inc.; Been and Cech, 1986, Cell, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in MC4-R.

As in the antisense approach, the ribozymes can be composed of modified oligonucleotides (e.g. for improved stability, targeting, etc.) and should be delivered to cells which express the MC4-R in vivo, e.g., hypothalamus. A preferred method of delivery involves using a DNA construct "encoding" the ribozyme under the control of a strong constitutive pol III or pol II promoter, so that transfected cells will produce sufficient quantities of the ribozyme to destroy endogenous MC4-R messages and inhibit translation. Because ribozymes unlike antisense molecules, are catalytic, a lower intracellular concentration is required for efficiency.

Endogenous MC4-r gene expression can also be reduced by inactivating or "knocking out" the MC4-r gene or its promoter using targeted homologous recombination (e.g., see Smithies et al., 1985, Nature 317:230–234; Thomas & Capecchi, 1987, Cell 51:503–512; Thompson et al., 1989 Cell 5:313–321; each of which is incorporated by reference herein in its entirety). For example, a mutant, non-functional MC4-R (or a completely unrelated DNA sequence) flanked by DNA homologous to the endogenous MC4-r gene can be used, with or without a selectable marker and/or a negative selectable marker, to transfect cells that express MC4-R in vivo. Insertion of the DNA construct, via targeted homologous recombination, results in inactivation of the MC4-r gene. Such approaches are particularly suited in the agricultural field where modifications to ES (embryonic stem) cells can be used to generate animal offspring with an inactive MC4-R (e.g., see Thomas & Capecchi 1987 and Thompson 1989, supra). However this approach can be adapted for use in humans provided the recombinant DNA constructs are directly administered or targeted to the required site in vivo using appropriate viral vectors, e.g., herpes virus vectors for delivery to brain tissue; e.g., the hypothalamus and/or choroid plexus.

Alternatively, endogenous MC4-R gene expression can be reduced by targeting deoxyribonucleotide sequences complementary to the regulatory region of the MC4-R gene (i.e., the MC4-R promoter and/or enhancers) to form triple helical structures that prevent transcription of the MC4-R gene in target cells in the body. (See generally, Helene, C. 1991, Anticancer Drug Des., 6(6):569–84; Helene, C., et al., 1992, Ann, N.Y. Acad. Sci., 660:27–36; and Maher, L. J., 1992, Bioassays 14(12):807–15).

5.4.3. DELIVERY OF SOLUBLE MC4-R POLYPEPTIDES

Genetically engineered cells that express soluble MC4-R ECDs or fusion proteins e.g. fusion Ig molecules can be administered in vivo where they may function as "bioreactors" that deliver a supply of the soluble molecules. Such soluble MC4-R polypeptides and fusion proteins, when expressed at appropriate concentrations, should neutralize or "mop up" the native ligand for MC4-R, and thus act as inhibitors of MC4-R activity and induce weight gain.

5.5. PHARMACEUTICAL FORMULATIONS AND METHODS OF TREATING BODY WEIGHT DISORDERS

The invention encompasses methods and compositions for modifying body weight and treating body weight disorders, including but not limited to obesity, cachexia and anorexia. Because a loss of normal MC4-R gene product function results in the development of an obese phenotype, an increase in MC4-R gene product activity, or activation of the MC4-R pathway (e.g., downstream activation) would facilitate progress towards a normal body weight state in obese individuals exhibiting a deficient level of MC4-R gene expression and/or MC4-R activity.

Alternatively, symptoms of certain body weight disorders such as, for example, cachexia, which involve a lower than normal body weight phenotype, may be ameliorated by decreasing the level of MC4-R gene expression, and/or MC4-R gene activity, and/or downregulating activity of the MC4-R pathway (e.g., by targeting downstream signalling events). Different approaches are discussed below.

Agonists of MC4-R can be used to induce weight loss for treating obesity. Antagonists of MC4-R activity can be used to induce weight gain for treating conditions such as anorexia or cachexia. It is not necessary that the compound demonstrate absolute specificity for the MC4-R. For example, compounds which agonize both MC4-R and MC1-R could be used; such compounds could be administered so that delivery to the brain is optimized to achieve weight reduction, and side effects, such as peripheral melanin production resulting in a "tan" may well be tolerated. Compounds which do not demonstrate a specificity for MC4-R can be administered in conjunction with another therapy or drug to control the side-effects that may result from modulating another melanocortin receptor; however, compounds which demonstrate a preference or selectivity for MC4-R over MC3-R are preferred since both receptors are expressed in the brain where localized delivery cannot be used to compensate for lack of receptor specificity.

5.5.1. DOSE DETERMINATIONS

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

5.5.2. FORMULATIONS AND USE

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

6. EXAMPLE

GENERATION OF AN MC4-R DEFICIENT MOUSE

The following example describes the engineering and generation of "knock-out" mice in which the endogenous MC4-r is inactivated. The results show that the knock-out mice gain weight, thus, demonstrating the role and function of the MC4-R in body weight regulation.

6.1. MATERIALS AND METHODS 6.1.1. IDENTIFICATION OF THE MURINE MC4-R GENE

The murine melanocortin 4 receptor (MC4-r) gene was isolated from a mouse strain 129/Sv genomic phage library, obtained from Stratagene, using a human MC4-r probe. The human probe was generated by PCR amplification of MC4-r coding sequences from human genomic DNA using the following primers:

5'-ATA GTC GAC ATG GTG AAC TCC ACC CAC CGT-3'; and

5'-TAT AAG CTT TTA ATA TCT GCT AGA CAA GTC-3'.

Two positive phage clones containing the MC4-r gene were identified, and the MC4-r locus was subcloned from phage into pBluescript II as an ~5 Kb Hind III fragment, and an ~4.7 Kb Sac I fragment. These subclones were restriction mapped and partially sequenced to produce the map of the MC4-r locus shown in FIG. 2A. In order to inactivate MC4-r, a targeting construct was built which would delete the majority of MC4-r coding sequences following homologous recombination with the endogenous MC4-r locus.

6.1.2. GENERATION OF THE TARGETING CONSTRUCT

The MC4-r targeting construct was constructed in the following manner. The 1.4 Kb Eco RI-Ava I fragment of pBR322 was replaced with the following synthetic oligonucleotides: 5'-AAT TAG CGG CCG CAG TAT GCA AAA AAA AGC CCG CTC ATT AGG CGG GCT-3' (SEQ ID NO: 7); and 5'-CCG AAG CCC GCC TAA TGA GCG GGC TTT TTT TTG CAT ACT GCG GCC GCT-3' (SEQ ID NO: 8). The resulting plasmid, called pJN1, was digested with Not I and the following oligonucleotides were ligated into the Not I site.

```
5'-GGC CGG CAT GCA TCA AGC TTA       (SEQ ID NO:9);

TCT CGA GAT CGT CGA CTA CCA TAC

ATC GAT CAG GTA CCA TCC CGG GGC-3';

and

5'GGC CGC CCC GGG ATG GTA CCT       (SEQ ID NO:10)

GAT CGA TGT ACC ATG GTA GTC GAC GAT

CTC GAG ATA AGC TTG ATG CAT GCC-3'.
```

The resulting plasmid was called pJN2.

The 1.2 Kb Sph I-Hind III fragment 3' of the MC4-r gene (see FIG. 2A) was subcloned into SphI-Hind III digested pJN2 to generate the plasmid MC4-r KO 3' (FIG. 2B). This fragment represents the 3' region of genomic homology in the targeting vector. A 3.4 Kb NcoI-Hind III fragment, including the first approximately 20 nucleotides of the MC4-r gene (see FIG. 2A), was excised as a NcoI-Asp718 fragment from the subclone MC4-r locus. The Asp718 site was derived from pBluescript II polylinker sequences immediately flanking the native Hind III site approximately 3.4 Kb 5' of the MC4-r gene (FIG. 2A). This fragment, which represents the 5' region of genomic homology in the targeting construct, was ligated into NcoI-Asp 718 digested MC4-r KO 5' to produce MC4-r KO 5'3' (FIG. 2C).

The PGK-neo expression cassette from the plasmid pKJ1 (Tybulewicz et al., Cell 65, 1153–1163, 1991), containing the neo gene under the transcriptional control of the mouse phosphoglycerate kinase (PGK-1) promoter and the PGK-1 poly(A) addition site, was subcloned as an Eco RI-Hind III fragment into EcoRI-Hind III digested pGEM 7-Zf(+) to generate pGEM 7 (KJ1). The 1.7 Kb fragment containing the PGK-neo expression cassette was excised by: 1) digestion of pGEM 7 (KJ1) with Xho I, which cuts in the polylinker 5' of the PGK promoter, and blunt end filling of the Xho I site with Klenow polymerase, and 2) digestion with Sca I which cuts within mouse genomic sequence 3' of the PGK polyadenylation signal. This fragment was ligated into Xho I digested MC4-r KO 5'3' which had also been blunt-ended with Klenow polymerase, to generate the MC4-r targeting vector MC4-r KO 5'3' neo (FIG. 2D). A schematic map of the gene targeting strategy for inactivation of the MC4-r locus with this vector is shown in FIGS. 3A–3D.

6.1.3. GENERATION OF TARGETED ES CELLS

The RF-8 ES cell line (obtained from the Gladstone Institute of Cardiovascular Disease, UCSF) was cultured on SNL76/7 mitotically inactive feeder cells as described in McMahon and Bradley (1990, Cell 62: 1073–1085). For electroporation, cells were trypsinized and resuspended at a concentration of $1.1 \times 10^7$/ml in PBS ($Ca^{2+}$ and $MG^{2+}$ free; Gibco). An 0.9 ml aliquot ($1 \times 10^7$ cells) was mixed with 20 µg of MC4-r KO 5'3' DNA, which had been linearized by Not I digestion, and pulsed at 250 V, 500 µF (Bio-Rad Gene Pulser), after which the cells were diluted in culture medium, plated at $1 \times 10^6$ per 100 mm plate containing feeder cells, and placed under selection twenty-four hours later in G418 sulfate (400 µg/ml powder, Gibco) for 6 days. 427 G418 resistant clones were picked, dissociated with trypsin and divided into one well each of two 96-well plates. Upon confluence, ES cells were frozen in one of the 96-well plates as described by Ramirez-Solis et al., (Methods in Enzymology, vol. 225, Wassarman, P. M., DePamphilis, M. L. (eds). Academic Press, p. 855–878, 1992) and expanded into a 24 well plate. Upon confluence, DNA was prepared for Southern blot analysis.

Genomic DNA was prepared in situ from ES cells in 24 well plates by the procedure of Laird et al. (1991, Nucleic Acids Research 19: 4293). To screen for homologous recombination between the vector and the endogenous MC4-r locus approximately 20 µg of genomic DNA was digested with Apa I, electrophoresed through a 1% agarose gel, transferred to Hybond $N^+$ membrane (Amersham), and hybridized with the $^{32}P$ radiolabeled Sac I-Sph I probe (see FIGS. 3A–3E).

6.1.4. GENERATION OF MC4-R DEFICIENT MICE

Clone 155 was injected into C57BL/6J blastocysts to generate chimeric mice as described in (Bradley, A. In Robertson, E. J. (ed) Teratocarcinomas and Embryonic Stem Cells. IRL Press, Oxford, England, p. 113–151, 1987). Male chimeras were bred with C57BL/6J females, and agouti offspring (representing germline transmission of the ES genome) were screened for the presence of the targeted MC4-r gene by Southern blot hybridization of Apa I as well as Nco I digested tail DNA using the probe shown in FIG. 3A. Offspring heterozygous for the mutation were identified by either the presence of a 7.6 Kb Apa I band in addition to the wild type 2.2 Kb band or the presence of a 1.9 Kb Nco I band in addition to the wild type bands of 2.6 Kb and 2.8 Kb (FIG. 3D).

Heterozygous mice were interbred and offspring generated by these matings were screened by Southern blot hybridization of Apa I as well as Nco I digested tail DNA. Mice homozygous for the deleted MC4-r gene were identified by the absence of the wild type 2.2 Kb Apa I band and 2.8 Kb Nco I band, and presence of the targeted 7.6 Kb Apa I band and 1.9 Kb Nco I band. To verify deletion of the MC4-r gene, the Apa I digested and Nco I digested blots were stripped and re-probed with the human MC4-r coding sequence. No hybridizing bands were observed in the DNA from mice homozygous for the MC4-r mutation, verifying the absence of the MC4-r gene in these mice.

6.1.4 WEIGHT AND LENGTH MEASUREMENTS

Weight gain was regularly measured, beginning at 3–4 weeks of age, using a Sartorius model #14800 P balance. Length was measured by manual immobilization and extension of the mouse to its full length, always by the same individual, and measurement of the nose to anus distance in centimeters.

6.1.5. FOOD CONSUMPTION

Food intake was measured for two $A_y$, two C57BL/6J, four MC4-R homozygous mutants, and four wild type F2 controls, each housed two to a cage. The mice were housed for at least a week before any measurements were taken. Over a two week period, a sufficient amount of food for the week was then weighed and provided to the mice ad libitum. Each weekday morning the remaining food was measured, for a total of eight measurements. Cages were carefully monitored for spillage, which was negligible. The $A_y$ and C57BL/6J mice were 9 weeks of age at the time measurement of food consumption was initiated; both the four MC4-R deficient mice and the F2 controls were each 15, 15, 17.5 and 20.5 weeks of age.

6.1.6. SERUM ANALYSIS

For glucose, insulin and leptin measurements, blood was collected by retroorbital sinus puncture from animals provided with food and water ad libi tum Mice were handled regularly (three times per week for several weeks) prior to bleeding to minimize stress, and cages were singly moved to a separation location at the time of bleeding. For measurement of glucose levels, 5 µl of serum was analyzed in a YSI Model 27 glucose analyzer (Yellow Springs Instrument Company, Inc.) using a glucose oxidase assay. Results are expressed as mg/dl. The range of detection if 0–500 mg/dl, with a coefficient of variation of <1%. Serum insulin concentration was measured in duplicate in a 10 µl volume by a specific competitive protein binding assay using rat insulin as the standard. Results are expressed as ng/ml. The range of detection is 0.1–25 ng/ml with a coefficient of variation of <10%. Leptin was measured in duplicate in 20 µl of serum using a radioimmunoassay kit to mouse leptin with recombinant mouse leptin as the standard (Linco Research,Inc.).

For serum corticosterone measurements, mice were housed at three animals per cage with food and water ad libitum. To prevent stress-mediated elevation of corticosterone levels mice were handled 2–3 times/day for three days prior to drawing blood. Cages were brought one at a time into a separate room, mice were weighed and then held as if blood were to be drawn. On the fourth day mice were handled similarly, and blood drawn between 8:00 and 9:00 A.M. within 30 sec of handling. Cages were not returned to the housing room until all the samples had been obtained. Blood was obtained by snipping the tail tip and collecting blood into a Multivette S Gel tube (Sarstedt). Tubes were placed on ice for 20–40 minutes and centrifuged 3–4 minutes at 14,000 rpm to separate the serum. Two one μl aliquots of serum from each sample were then assayed for corticosterone levels using an ImmuChem Double Antibody Corticosterone 125I RIA kit (ICN Biomedicals, Inc.)

6.1.7. HISTOLOGY

For in situ hybridization analysis of POMC gene expression, wild type, heterozygous, and homozygous mutant mice were maintained under a 12-h light, 12-h dark cycle at constant temperature. Food (Purina mouse chow) and water were provided ad libitum. Anesthetized (avertin) animals were sacrificed between 1500 and 1700 hrs. before lights out via cardiac puncture and perfusion with saline (20 mls) and then 50 mls of ice-cold fixation buffer (4% paraformaldehyde in borate buffer, pH 9.5). Whole brains were rapidly removed and then post-fixed overnight in 10% sucrose/fixative buffer. Blocked hypothalamic sections were frozen in powdered dry ice and then stored at −80° C. prior to sectioning.

Antisense POMC probe was prepared by linearizing the plasmid mPOMCE3ribo (kindly provided by Dr. Malcolm Low), containing exon 3 of the mouse POMCd gene, with Nco I. [$^{35}$S] cRNA probes were prepared by transcribing 1 μg of each linearized DNA with T7 DNA polymerase for 1 hr at 37° C. as described (Promega). Hypothalamic brain blocks were mounted on a frozen stage and serially sectioned into 4 series of 20-μM slices with a sliding microtome. Sections were prepared and hybridized for 20 h at 58° C. with $^{35}$S-labeled probes ($5 \times 10^6$ cpm/ml) in 65% formamide, 0.26M NaCl, 1.3x Denhardt's solution, 1.3 mM EDTA, 13% dextran sulfate, 13 mM Tris, pH 8. Sections were then digested with RNase (20 μg/ml) for 30 min at 37° C., and then desalted in a series of washes from 4x SSC/1 mM DTT to a final stringency of 0.1x SSC/1 mM DTT at 65° C. for 30 min. Sections were dehydrated in ascending ethanol, vacuum dried at room temp for 30 min, and then exposed to Dupont Cronex film for several days. Dried slides were then dipped in NTB-2 emulsion (Kodak), and developed after 6 days.

6.2. RESULTS 6.2.1. GENERATION OF MC4-R DEFICIENT MICE

The murine MC4-R gene consists of approximately 1 kb of coding sequence contained within a single exon (FIGS. 1A–1B). A targeting vector was designed to delete virtually all MC4-R coding sequence following homologous recombination with the locus in embryonic stem (ES) cells. As shown in FIGS. 1A–1B the vector consists of a total of approximately 4.5 kb of strain 129/Sv mouse genomic DNA flanking a deletion of 1.5 kb. This deletion extends from the Nco I site located approximately 20 nucleotides downstream of the MC4-R initiation codon to the Hind III site situated approximately 0.5 kb 3' of the gene. The deleted MC4-R sequences have been replaced by the neo gene under the control of the phosphoglycerate kinase-1 (PGK-1) promoter.

A total of 809 G418-resistant colonies were screened for homologous recombination by Southern blot hybridization of Apa I digested genomic DNA with the flanking probe shown in FIG. 3A. One clone showed the predicted 7.6 kb targeted Apa I DNA fragment in addition to the expected 2.2 kb wild type fragment. Injection of this clone into C57BL/6J blastocysts produced several male chimeras which, when bred to C57BL/6J females, transmitted the targeted MC4-R allele to their F1 129/B6 offspring. F1 heterozygotes were interbred and their offspring genotyped by Southern blot hybridization of Apa I or Nco I digested tail DNA with the flanking probe. As described above, Apa I digestion generates a wild type fragment of 2.2 kb and a targeted fragment of 7.6 kb (note that this 7.6 kb is distinct from a background band of slightly lower molecular weight which is present in all samples; FIG. 3A). Nco I digestion generates two wild type fragments of 2.7 and 2.9 kb, since the Nco I site is situated within the sequences recognized by the flanking probe (FIG. 3A). The 2.7 kb Nco I fragment represents genomic sequences extending 3' of the probe which are unaffected by MC4-R targeting, whereas the 2.9 kb band includes the MC4-R gene sequences. Following targeting, this latter fragment is reduced to a 2 kb band diagnostic of the mutated MC4-R allele. As shown in FIG. 3E, heterozygous intercrosses produced homozygous mutant, heterozygous and wild type F2 progeny. To verify deletion of the MC4-R gene in homozygous mutants, the filters were stripped and rehybridized with an MC4-R probe. No MC4-R hybridization was detected in homozygous mutant mice, whereas the predicted 2.2 kb and 5.1 kb Apa I bands (Apa I cuts within the MC4-R gene generating two MC4-R-containing fragments; see FIG. 3A) and 2.9 kb Nco I fragment were observed in both heterozygous and wild type littermates (FIG. 3E).

6.2.2. BODY WEIGHT AND SIZE OF MC4-R DEFICIENT MICE

F2 animals were maintained on a chow diet ad libitum and their weights monitored regularly. The weights of MC4-R deficient mice and their wild type littermates were largely indistinguishable for the first 4 weeks of life. However, by approximately 5 weeks of age most of the homozygous mutants, both males and females, were heavier than their wild type siblings of the same sex, and by 7 weeks of age all of the null mutants were heavier than the controls (FIGS. 4A and 4C). By 15 weeks of age, homozygous mutant females were on average twice as heavy as their wild type siblings, while homozygous mutant males were approximately 50% heavier than wild type controls. Weight gain for both males and female mutant mice appeared to be approaching a plateau by about 24 weeks of age at which time the weight of female null mice averaged approximately 63 grams (n=3), and males averaged approximately 65 grams (n=8). Mice heterozygous for MC4-R deletion showed a weight gain intermediate to that seen in wild type and homozygous mutant sibs (FIGS. 4B and 4D), demonstrating a gene dosage effect of MC4-R ablation on body weight regulation.

One of the distinguishing characteristics of the obese yellow phenotype is an increase in skeletal growth. Typically, A$^y$ mice are on average approximately 5% longer than their wild type siblings (Castle, 1941, Genetics 26:177191; Carpenter and Mayer, 1958, Am. J. Physiol. 193:499–504). To determine whether mice lacking the MC4-R exhibit enhanced linear growth, body length measurements of F2 progeny were taken at approximately 19 weeks of age (between 132–138 days). As shown in FIG. 6, MC4-R deficient mice are significantly longer than wild type controls. The mean length of homozygous mutant females is increased approximately 11% relative to wild type F2 mice, and heterozygous females are approximately 7%longer than controls. Male homozygotes and heterozygotes are approximately 8% and 2.5% longer than controls, respectively.

6.2.3. FOOD CONSUMPTION

To determine whether food consumption was increased in mice lacking the MC4-R, homozygous mutant females and wild type F2 controls were monitored for food intake over a 2 week period. A$^y$ mutants, on a C57BL/6J background, and C57BL/6J controls were also monitored. As previously documented (Frigeri et al., 1988, Endocrinology 113:2097–2105; Shimizu et al., 1989, Life Sciences 45:543–552), A$^y$ mice were hyperphagic, eating 36% more than C57BL/6J controls. Similarly, absence of the MC4-R also resulted in a significant increase (46%) in food consumption over wild type F2 controls (FIG. 7).

6.2.4. SERUM ANALYSIS

Blood was collected from MC4-R deficient mice and wild type controls over three time intervals (4–8 weeks, 10–14 weeks, 17–23 weeks) and serum assayed for glucose and insulin levels. Serum glucose levels were essentially unchanged in females heterozygous or homozygous for MC4-R deletion, but both heterozygous and homozygous males were hyperglycemic (FIGS. 8A and 8B). This was first evident for homozygous males at the 10–24 week interval at which time glucose levels were elevated over 2 fold above controls, to 390 mg/dl, but heterozygous mutants showed only a slight elevation of serum glucose at this age. By 17–23 weeks of age, both heterozygous and homozygous male mutant mice showed a doubling of normal serum glucose levels (334 and 361 mg/dl, respectively) relative to controls (156 mg/dl).

Both male and female mutant mice were hyperinsulinemic (FIGS. 8C and 8D). Nine fold and 5 fold increases in insulin levels were evident in the sera of homozygous mutant females and males, respectively, at 4–8 weeks of age. These levels increased dramatically over time, such that by 17–23 weeks of age the mean concentration of insulin in the serum of homozygous mutant females was approximately 65 ng/ml, and for males approximately 130 ng/ml, representing approximately 60 and 14 fold increases, respectively, over insulin levels in F2 wild type controls. Heterozygous mutants were also hyperinsulinemic, although less so than homozygous mutants. For both male and female heterozygotes, a significant difference in insulin levels relative to controls was first observed at the 10–14 week interval; by 17–23 weeks mean insulin levels of heterozygotes were elevated to approximately 10 ng/ml (females) and 85 ng/ml (males).

In addition to glucose and insulin, serum leptin and corticosterone levels were also determined. Leptin levels are elevated in A$^y$ mice (Maffei et al., 1995, Nat. Med. 1:1155–1161; Mizuno et al., 1996, Proc. Natl. Acad. Sci. 93:3434–3438), indicating that the syndrome does not result from defects in leptin production. Consistent with postulated role of the hormone in signaling fat depot levels (Campfield et al., 1995, Science 269:546–549; Halaas et al., 1995, Science 269:543–546; Pelleymounter et al., 1995, Science 269:540–543), leptin is also elevated in MC4-R deficient mice (FIGS. 8E and 8F). At 4–8 weeks of age leptin was elevated 4.5 fold and 1.5 fold in the serum of female and male homozygous mutants, respectively, relative to wild type controls. By 17–23 weeks of age serum leptin levels in females had reached approximately 97 ng/ml, in males approximately 58 ng/ml, representing increases of 6.5 and 2.5 fold, respectively. Heterozygous mice, for the most part, showed leptin levels intermediate between that observed for wild type mice and homozygous mutants.

Since glucocorticoids can profoundly effect weight homeostasis and somatic growth, basal serum corticosterone was measured in three sets of sex-matched littermates, each containing a wild-type, heterozygous, and homozygous mutant animal (FIG. 9). No effect of MC4-R gene knockout on basal corticosterone levels was detected.

6.2.5. POMC GENE EXPRESSION

To assess whether the observed effects of MC4-R deletion on weight homeostasis could be attributed to the induction of compensatory changes in the sole known source of ligand for the MC4-R, the POMC gene, central POMC gene expression was examined in wild type mice, mice heterozygous for MC4-R deletion and homozygous mutants by in situ hybridization (FIGS. 10A–10F). No new sites of POMC gene expression and no consistent change in the levels of POMC mRNA in its primary site of expression, the arcuate nucleus of the hypothalamus, were detected by this assay. In addition, no gross neuroanatomical defects were observed in thionin-stained brain sections from heterozygous or homozygous mutant MC4-R deficient animals by histological analysis (FIGS. 10A–10C).

7. EXAMPLE

AGOUTI PROTEIN BINDS DIRECTLY TO MC1-R AND MC4-R

The following example describes experiments demonstrating that the Agouti protein binds directly to the melanocortin receptors.

7.1. MATERIAL AND METHODS

Human melanocortin receptor 4 (hMC4-r) cDNA, under the control of the CMV promoter, was transfected into the 293 cell line, and stable clones were selected (293/MC4-R). The stable clones were tested for reduction in intracellular cAMP levels in the presence of 5 nM agouti protein.

COS-7 cells were transfected with hMC1-r or hMC4-r by the DEAE-Dextran method. A plasmid containing the Adenovirus VA1 and VA2 RNA genes was used to co-transfect the COS cells to enhance transient protein expression by increasing translational initiation. The MC4-r and the VA1/2 cDNA plasmids were used at a ratio of 10 to 1. Control plates received the VA1/2 plasmid alone. 48 hours post-transfection, the cells were rinsed and culture supernatant containing 15 nM of AP-Ag was added. AP-Ag is a truncated agouti protein, containing the cysteine-rich domain tagged with the alkaline phosphatase at its N-terminal. Binding of AP-Ag to transfected cells proceeded at room temperature for 90 minutes with gentle rocking. The cells were then washed 7 times before fixing and color development using NBT/BCIP substrate.

7.2. RESULTS

When 5 nM agouti protein was added to the 293/MC4-R line, an 18% reduction of intracellular cAMP level, relative to the parental 293 cell line, was observed. The results indicate that MC4-R mediates the agouti-triggered decrease of intracellular cAMP level and confers agouti response to 293 cells.

N-terminal truncated agouti protein, containing only the cysteine-rich C-terminal domain, retains the antagonizing activity of the full-length agouti. A truncated agouti protein, containing only the cysteine-rich domain and tagged with the alkaline phosphatase at its N-terminal, was used to assay the direct binding between the agouti protein and the MC1 and MC4 receptors in COS7 cells.

The transfection efficiency, as monitored by β-galactosidase reporter plasmid, typically was 12–16%. 10–13% of the MC1-r transfected and 3–4% of the MC4-r transfected COS7 cells bound the agouti protein as determined by AP staining. The observed difference in percentage of positive cell between the MC1-r and MC4-r transfected COS7 cells could be attributed to differences in binding affinity and/or expression level.

To assess the affinity of the agouti protein for the MC1-R receptor, a Scatchard Analysis was performed on MC1-r transfected COS7 cells using culture supernatant containing up to 30 nM AP-Ag. The Kd has been estimated at 20–30 nM range.

7.3. DISCUSSION

The dominant agouti alleles that give rise to obesity result from constitutive deregulated synthesis of wild-type agouti protein throughout the animal, and presumably accounts for the other characteristics of the pleiotropic obesity syndrome such as hyperphagia, hyperinsulinemia, and hyperglycemia. One possible mechanism by which ectopic agouti expression induces obesity is aberrant antagonism of melanocortin receptors, such as MC4-R, expressed in regions of the brain known to be involved in regulating feeding.

The data presented herein demonstrates that the Agouti protein binds directly to MC4-R. Furthermore, as described in Example 6, supra, transgenic mice lacking the MC4-R produce an obesity syndrome that strikingly resembles the agouti syndrome. The recapitulation of many of the features of the agouti syndrome in MC4-R deficient mice demonstrates that antagonism of melanocortin signaling via MC4-R is the primary cause of the agouti obesity syndrome.

The present invention is not to be limited in scope by the specific embodiments described which are intended as single illustrations of individual aspects of the invention, and functionally equivalent methods and components are within the scope of the invention. Indeed various modifications of the invention, in addition to those shown and described herein will become apparent to those skilled in the art from the foregoing description and accompanying drawings. Such modifications are intended to fall within the scope of the appended claims.

What is claimed is:

1. A transgenic mouse comprising a mutation in an endogenous melanocortin-4-receptor (MC4-R) gene, wherein
   (1) said mutation has been introduced into said mouse by homologous recombination in a mouse embryonic stem cell; and
   (2) said mutation inactivates said gene and results in the lack of expression of a functional MC4-R protein;
   and further wherein said mutation results in said mouse having maturity onset obesity syndrome.

2. A progeny mouse of the transgenic mouse of claim 1, wherein said progeny mouse contains said mutation that inactivates said MC4-R gene and results in the lack of expression of a functional MC4-R protein; and further wherein said mutation results in said progeny mouse having maturity onset obesity syndrome.

3. The mouse of claim 1 or 2 wherein one or more of the exons of said MC4-R gene have been deleted.

4. The mouse of claim 1 or 2 wherein a heterologous DNA sequence has been introduced into one or more of the exons of said MC4-R gene.

5. The mouse of claim 4 wherein said DNA sequence comprises one or more stop codons.

\* \* \* \* \*

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 360 amino acids
      (B) TYPE: amino acid
      (C) STRANDEDNESS:
      (D) TOPOLOGY: unknown (ii) MOLECULE TYPE: peptide (xi) SEQUENCE DESCRIPTION: SEQ ID NO:1:

```
Met Ser Ile Gln Lys Lys Tyr Leu Glu Gly Asp Phe Val Phe Pro Val
 1               5                  10                  15

Ser Ser Ser Ser Phe Leu Arg Thr Leu Leu Glu Pro Gln Leu Gly Ser
                20                  25                  30

Ala Leu Leu Thr Ala Met Asn Ala Ser Cys Cys Leu Pro Ser Val Gln
            35                  40                  45

Pro Thr Leu Pro Asn Gly Ser Glu His Leu Gln Ala Pro Phe Phe Ser
        50                  55                  60

Asn Gln Ser Ser Ser Ala Phe Cys Glu Gln Val Phe Ile Lys Pro Glu
65                  70                  75                  80

Ile Phe Leu Ser Leu Gly Ile Val Ser Leu Leu Glu Asn Ile Leu Val
                85                  90                  95

Ile Leu Ala Val Val Arg Asn Gly Asn Leu His Ser Pro Met Tyr Phe
            100                 105                 110

Phe Leu Cys Ser Leu Ala Val Ala Asp Met Leu Val Ser Val Ser Asn
        115                 120                 125

Ala Leu Glu Thr Ile Met Ile Ala Ile Val His Ser Asp Tyr Leu Thr
        130                 135                 140

Phe Glu Asp Gln Phe Ile Gln His Met Asp Asn Ile Phe Asp Ser Met
145                 150                 155                 160

Ile Cys Ile Ser Leu Val Ala Ser Ile Cys Asn Leu Leu Ala Ile Ala
                165                 170                 175

Val Asp Arg Tyr Val Thr Ile Phe Tyr Ala Leu Arg Tyr His Ser Ile
            180                 185                 190

Met Thr Val Arg Lys Ala Leu Thr Leu Ile Val Ala Ile Trp Val Cys
        195                 200                 205
```

-continued

```
Cys Gly Val Cys Gly Val Val Phe Ile Val Tyr Ser Glu Ser Lys Met
    210                 215                 220

Val Ile Val Cys Leu Ile Thr Met Phe Phe Ala Met Met Leu Leu Met
225                 230                 235                 240

Gly Thr Leu Tyr Val His Met Phe Leu Phe Ala Arg Leu His Val Lys
                245                 250                 255

Arg Ile Ala Ala Leu Pro Pro Ala Asp Gly Val Ala Pro Gln Gln His
            260                 265                 270

Ser Cys Met Lys Gly Ala Val Thr Ile Thr Ile Leu Leu Gly Val Phe
        275                 280                 285

Ile Phe Cys Trp Ala Pro Phe Phe Leu His Leu Val Leu Ile Ile Thr
    290                 295                 300

Cys Pro Thr Asn Pro Tyr Cys Ile Cys Tyr Thr Ala His Phe Asn Thr
305                 310                 315                 320

Tyr Leu Val Leu Ile Met Cys Asn Ser Val Ile Asp Pro Leu Ile Tyr
                325                 330                 335

Ala Phe Arg Ser Leu Glu Leu Arg Asn Thr Phe Arg Glu Ile Leu Cys
            340                 345                 350

Gly Cys Asn Gly Met Asn Leu Gly
            355                 360
```

(2) INFORMATION FOR SEQ ID NO:2:

(i) SEQUENCE CHARACTERISTICS:
        (A) LENGTH: 332 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:2:

```
Met Val Asn Ser Thr His Arg Gly Met His Thr Ser Leu His Leu Trp
1               5                   10                  15

Asn Arg Ser Ser Tyr Arg Leu His Ser Asn Ala Ser Glu Ser Leu Gly
                20                  25                  30

Lys Gly Tyr Ser Asp Gly Gly Cys Tyr Glu Gln Leu Phe Val Ser Pro
        35                  40                  45

Glu Val Phe Val Thr Leu Gly Val Ile Ser Leu Leu Glu Asn Ile Leu
50                  55                  60

Val Ile Val Ala Ile Ala Lys Asn Lys Asn Leu His Ser Pro Met Tyr
65                  70                  75                  80

Phe Phe Ile Cys Ser Leu Ala Val Ala Asp Met Leu Val Ser Val Ser
                85                  90                  95

Asn Gly Ser Glu Thr Ile Ile Ile Thr Leu Leu Asn Ser Thr Asp Thr
                100                 105                 110

Asp Ala Gln Ser Phe Thr Val Asn Ile Asp Asn Val Ile Asp Ser Val
            115                 120                 125

Ile Cys Ser Ser Leu Leu Ala Ser Ile Cys Ser Leu Leu Ser Ile Ala
        130                 135                 140

Val Asp Arg Tyr Phe Thr Ile Phe Tyr Ala Leu Gln Tyr His Asn Ile
145                 150                 155                 160

Met Thr Val Lys Arg Val Gly Ile Ile Ile Ser Cys Ile Trp Ala Ala
                165                 170                 175

Cys Thr Val Ser Gly Ile Leu Phe Ile Ile Tyr Ser Asp Ser Ser Ala
                180                 185                 190

Val Ile Ile Cys Leu Ile Thr Met Phe Phe Thr Met Leu Ala Leu Met
```

```
                195                 200                 205
Ala Ser Leu Tyr Val His Met Phe Leu Met Ala Arg Leu His Ile Lys
    210                 215                 220

Arg Ile Ala Val Leu Pro Gly Thr Gly Ala Ile Arg Gln Gly Ala Asn
225                 230                 235                 240

Met Lys Gly Ala Ile Thr Leu Thr Ile Leu Ile Gly Val Phe Val Val
                245                 250                 255

Cys Trp Ala Pro Phe Phe Leu His Leu Ile Phe Tyr Ile Ser Cys Pro
                260                 265                 270

Gln Asn Pro Tyr Cys Val Cys Phe Met Ser His Phe Asn Leu Tyr Leu
            275                 280                 285

Ile Leu Ile Met Cys Asn Ser Ile Ile Asp Pro Leu Ile Tyr Ala Leu
    290                 295                 300

Arg Ser Gln Glu Leu Arg Lys Thr Phe Lys Glu Ile Ile Cys Cys Tyr
305                 310                 315                 320

Pro Leu Gly Gly Leu Cys Asp Leu Ser Ser Arg Tyr
                325                 330
```

(2) INFORMATION FOR SEQ ID NO:3:

(i) SEQUENCE CHARACTERISTICS:
        (A) LENGTH: 297 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:3:

```
Met Lys His Ile Ile Asn Ser Tyr Glu Asn Ile Asn Asn Thr Ala Arg
1               5                   10                  15

Asn Asn Ser Asp Cys Pro Arg Val Val Leu Pro Glu Glu Ile Phe Phe
            20                  25                  30

Thr Ile Ser Ile Val Gly Val Leu Glu Asn Leu Ile Val Leu Leu Ala
        35                  40                  45

Val Phe Lys Asn Lys Asn Leu Gln Ala Pro Met Tyr Phe Phe Ile Cys
    50                  55                  60

Ser Leu Ala Ile Ser Asp Met Leu Gly Ser Leu Tyr Lys Ile Leu Glu
65                  70                  75                  80

Asn Ile Leu Ile Ile Leu Arg Asn Met Gly Tyr Leu Lys Pro Arg Gly
                85                  90                  95

Ser Phe Glu Thr Thr Ala Asp Asp Ile Ile Asp Ser Leu Phe Val Leu
                100                 105                 110

Ser Leu Leu Gly Ser Ile Phe Ser Leu Ser Val Ile Ala Ala Asp Arg
            115                 120                 125

Tyr Ile Thr Ile Phe His Ala Leu Arg Tyr His Ser Ile Val Thr Met
    130                 135                 140

Arg Arg Thr Val Val Val Leu Thr Val Ile Trp Thr Phe Cys Thr Gly
145                 150                 155                 160

Thr Gly Ile Thr Met Val Ile Phe Ser His His Val Pro Thr Val Ile
                165                 170                 175

Thr Phe Thr Ser Leu Phe Pro Leu Met Leu Val Phe Ile Leu Cys Leu
                180                 185                 190

Tyr Val His Met Phe Leu Leu Ala Arg Ser His Thr Arg Lys Ile Ser
            195                 200                 205

Thr Leu Pro Arg Ala Asn Met Lys Gly Ala Ile Thr Leu Thr Ile Leu
    210                 215                 220
```

```
Leu Gly Val Phe Ile Phe Cys Trp Ala Pro Phe Val His Val Leu
225                 230                 235                 240

Leu Met Thr Phe Cys Pro Ser Asn Pro Tyr Cys Ala Cys Tyr Met Ser
            245                 250                 255

Leu Phe Gln Val Asn Gly Met Leu Ile Met Cys Asn Ala Val Ile Asp
            260                 265                 270

Pro Phe Ile Tyr Ala Phe Arg Ser Pro Glu Leu Arg Asp Ala Phe Lys
            275                 280                 285

Lys Met Ile Phe Cys Ser Arg Tyr Trp
            290                 295
```

(2) INFORMATION FOR SEQ ID NO:4:

(i) SEQUENCE CHARACTERISTICS:
        (A) LENGTH: 317 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:4:

```
Met Ala Val Gln Gly Ser Gln Arg Arg Leu Leu Gly Ser Leu Asn Ser
1               5                   10                  15

Thr Pro Thr Ala Ile Pro Gln Leu Gly Leu Ala Ala Asn Gln Thr Gly
            20                  25                  30

Ala Arg Cys Leu Glu Val Ser Ile Ser Asp Gly Leu Phe Leu Ser Leu
            35                  40                  45

Gly Leu Val Ser Leu Val Glu Asn Ala Leu Val Val Ala Thr Ile Ala
50                  55                  60

Lys Asn Arg Asn Leu His Ser Pro Met Tyr Cys Phe Ile Cys Cys Leu
65                  70                  75                  80

Ala Leu Ser Asp Leu Leu Val Ser Gly Thr Asn Val Leu Glu Thr Ala
            85                  90                  95

Val Ile Leu Leu Leu Glu Ala Gly Ala Leu Val Ala Arg Ala Ala Val
            100                 105                 110

Leu Gln Gln Leu Asp Asn Val Ile Asp Val Ile Thr Cys Ser Ser Met
            115                 120                 125

Leu Ser Ser Leu Cys Phe Leu Gly Ala Ile Ala Val Asp Arg Tyr Ile
130                 135                 140

Ser Ile Phe Tyr Ala Leu Arg Tyr His Ser Ile Val Thr Leu Pro Arg
145                 150                 155                 160

Ala Arg Gln Ala Val Ala Ala Ile Trp Val Ala Ser Val Val Phe Ser
            165                 170                 175

Thr Leu Phe Ile Ala Tyr Tyr Asp His Val Ala Val Leu Leu Cys Leu
            180                 185                 190

Val Val Phe Phe Leu Ala Met Leu Val Leu Met Ala Val Leu Tyr Val
            195                 200                 205

His Met Leu Ala Arg Ala Cys Gln His Ala Gln Gly Ile Ala Arg Leu
            210                 215                 220

His Lys Arg Gln Arg Pro Val His Gln Gly Phe Gly Leu Lys Gly Ala
225                 230                 235                 240

Val Thr Leu Thr Ile Leu Leu Gly Ile Phe Phe Leu Cys Trp Gly Pro
            245                 250                 255

Phe Phe Leu His Leu Thr Leu Ile Val Leu Cys Pro Glu His Pro Thr
            260                 265                 270
```

```
Cys Gly Cys Ile Phe Lys Asn Phe Asn Leu Phe Leu Ala Leu Ile Ile
          275                 280                 285

Cys Asn Ala Ile Ile Asp Pro Leu Ile Tyr Ala Phe His Ser Gln Glu
          290                 295                 300

Leu Arg Arg Thr Leu Lys Glu Val Leu Thr Cys Ser Trp
305                 310                 315
```

(2) INFORMATION FOR SEQ ID NO:5:

(i) SEQUENCE CHARACTERISTICS:
        (A) LENGTH: 1671 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 394...1389
        (D) OTHER INFORMATION:

(xi) SEQUENCE DESCRIPTION: SEQ ID NO:5:

```
AGCTTCCGAG AGGCAGCCGA TGTGAGCATG TGCGCACAGA TTCGTCTCCC AATGGCATGG      60

CAGCTTCAAG GAAAATTATT TTGAACAGAC TTGAATGCAT AAGATTAAAG TTAAAGCAGA     120

AGTGAGAACA AGAAAGCAAA GAGCAGACTC TTTCAACTGA GAATGAATAT TTTGAAGCCC     180

AAGATTTTAA AGTGATGATG ATTAGAGTCG TACCTAAAAG AGACTAAAAA CTCCATGTCA     240

AGCTCTGGAC TTGTGACATT TACTCACAGC AGGCATGGCA ATTTTAGCCT CACAACTTTC     300

AGACAGATAA AGACTTGGAG GAAATAACTG AGACGACTCC CTGACCCAGG AGGTTAAATC     360

AATTCAGGGG GACACTGGAA TTCTCCTGCC AGC ATG GTG AAC TCC ACC CAC CGT     414
                                    Met Val Asn Ser Thr His Arg
                                      1               5

GGG ATG CAC ACT TCT CTG CAC CTC TGG AAC CGC AGC AGT TAC AGA CTG     462
Gly Met His Thr Ser Leu His Leu Trp Asn Arg Ser Ser Tyr Arg Leu
         10                  15                  20

CAC AGC AAT GCC AGT GAG TCC CTT GGA AAA GGC TAC TCT GAT GGA GGG     510
His Ser Asn Ala Ser Glu Ser Leu Gly Lys Gly Tyr Ser Asp Gly Gly
     25                  30                  35

TGC TAC GAG CAA CTT TTT GTC TCT CCT GAG GTG TTT GTG ACT CTG GGT     558
Cys Tyr Glu Gln Leu Phe Val Ser Pro Glu Val Phe Val Thr Leu Gly
 40                  45                  50                  55

GTC ATC AGC TTG TTG GAG AAT ATC TTA GTG ATT GTG GCA ATA GCC AAG     606
Val Ile Ser Leu Leu Glu Asn Ile Leu Val Ile Val Ala Ile Ala Lys
                 60                  65                  70

AAC AAG AAT CTG CAT TCA CCC ATG TAC TTT TTC ATC TGC AGC TTG GCT     654
Asn Lys Asn Leu His Ser Pro Met Tyr Phe Phe Ile Cys Ser Leu Ala
             75                  80                  85

GTG GCT GAT ATG CTG GTG AGC GTT TCA AAT GGA TCA GAA ACC ATT ATC     702
Val Ala Asp Met Leu Val Ser Val Ser Asn Gly Ser Glu Thr Ile Ile
         90                  95                 100

ATC ACC CTA TTA AAC AGT ACA GAT ACG GAT GCA CAG AGT TTC ACA GTG     750
Ile Thr Leu Leu Asn Ser Thr Asp Thr Asp Ala Gln Ser Phe Thr Val
    105                 110                 115

AAT ATT GAT AAT GTC ATT GAC TCG GTG ATC TGT AGC TCC TTG CTT GCA     798
Asn Ile Asp Asn Val Ile Asp Ser Val Ile Cys Ser Ser Leu Leu Ala
120                 125                 130                 135

TCC ATT TGC AGC CTG CTT TCA ATT GCA GTG GAC AGG TAC TTT ACT ATC     846
Ser Ile Cys Ser Leu Leu Ser Ile Ala Val Asp Arg Tyr Phe Thr Ile
                140                 145                 150

TTC TAT GCT CTC CAG TAC CAT AAC ATT ATG ACA GTT AAG CGG GTT GGG     894
Phe Tyr Ala Leu Gln Tyr His Asn Ile Met Thr Val Lys Arg Val Gly
            155                 160                 165
```

```
ATC AGC ATA AGT TGT ATC TGG GCA GCT TGC ACG GTT TCA GGC ATT TTG      942
Ile Ser Ile Ser Cys Ile Trp Ala Ala Cys Thr Val Ser Gly Ile Leu
            170                 175                 180

TTC ATC ATT TAC TCA GAT AGT AGT GCT GTC ATC ATC TGC CTC ATC ACC      990
Phe Ile Ile Tyr Ser Asp Ser Ser Ala Val Ile Ile Cys Leu Ile Thr
185                 190                 195

ATG TTC TTC ACC ATG CTG GCT CTC ATG GCT TCT CTC TAT GTC CAC ATG     1038
Met Phe Phe Thr Met Leu Ala Leu Met Ala Ser Leu Tyr Val His Met
200                 205                 210                 215

TTC CTG ATG GCC AGG CTT CAC ATT AAG AGG ATT GCT GTC CTC CCC GGC     1086
Phe Leu Met Ala Arg Leu His Ile Lys Arg Ile Ala Val Leu Pro Gly
                220                 225                 230

ACT GGT GCC ATC CGC CAA GGT GCC AAT ATG AAG GGA GCG ATT ACC TTG     1134
Thr Gly Ala Ile Arg Gln Gly Ala Asn Met Lys Gly Ala Ile Thr Leu
            235                 240                 245

ACC ATC CTG ATT GGC GTC TTT GTT GTC TGC TGG GCC CCA TTC TTC CTC     1182
Thr Ile Leu Ile Gly Val Phe Val Val Cys Trp Ala Pro Phe Phe Leu
250                 255                 260

CAC TTA ATA TTC TAC ATC TCT TGT CCT CAG AAT CCA TAT TGT GTG TGC     1230
His Leu Ile Phe Tyr Ile Ser Cys Pro Gln Asn Pro Tyr Cys Val Cys
265                 270                 275

TTC ATG TCT CAC TTT AAC TTG TAT CTC ATA CTG ATC ATG TGT AAT TCA     1278
Phe Met Ser His Phe Asn Leu Tyr Leu Ile Leu Ile Met Cys Asn Ser
280                 285                 290                 295

ATC ATC GAT CCT CTG ATT TAT GCA CTC CGG AGT CAA GAA CTG AGG AAA     1326
Ile Ile Asp Pro Leu Ile Tyr Ala Leu Arg Ser Gln Glu Leu Arg Lys
                300                 305                 310

ACC TTC AAA GAG ATC ATC TGT TGC TAT CCC CTG GGA GGC CTT TGT GAC     1374
Thr Phe Lys Glu Ile Ile Cys Cys Tyr Pro Leu Gly Gly Leu Cys Asp
            315                 320                 325

TTG TCT AGC AGA TAT TAAATGGGGA CAGAGCACGC AATATAGGAA CATGCATAAG A   1430
Leu Ser Ser Arg Tyr
            330

GACTTTTTCA CTCTTACCCT ACCTGAATAT TGTACTTCTG CAACAGCTTT CTCTTCCGTG   1490

TAGGGTACTG GTTGAGATAT CCATTGTGTA AATTTAAGCC TATGATTTTT AATGAGAAAA   1550

AATGCCCAGT CTCTGTATTA TTTCCAATGT CATGCTACTT TTTTGGCCAT AAAATATGAA   1610

TCTATGTTAT AGGTTGTAGG CACTGTGGAT TTACAAAAAG AAAAGTCCTT ATTAAAAGCT   1670

T                                                                  1671

(2) INFORMATION FOR SEQ ID NO:6:

(i) SEQUENCE CHARACTERISTICS:
        (A) LENGTH: 332 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:6:

Met Val Asn Ser Thr His Arg Gly Met His Thr Ser Leu His Leu Trp
1               5                   10                  15

Asn Arg Ser Ser Tyr Arg Leu His Ser Asn Ala Ser Glu Ser Leu Gly
            20                  25                  30

Lys Gly Tyr Ser Asp Gly Gly Cys Tyr Glu Gln Leu Phe Val Ser Pro
        35                  40                  45

Glu Val Phe Val Thr Leu Gly Val Ile Ser Leu Leu Glu Asn Ile Leu
50                  55                  60
```

```
Val Ile Val Ala Ile Ala Lys Asn Lys Asn Leu His Ser Pro Met Tyr
 65                  70                  75                  80

Phe Phe Ile Cys Ser Leu Ala Val Ala Asp Met Leu Val Ser Val Ser
                 85                  90                  95

Asn Gly Ser Glu Thr Ile Ile Thr Leu Leu Asn Ser Thr Asp Thr
            100                 105                 110

Asp Ala Gln Ser Phe Thr Val Asn Ile Asp Asn Val Ile Asp Ser Val
            115                 120                 125

Ile Cys Ser Ser Leu Leu Ala Ser Ile Cys Ser Leu Leu Ser Ile Ala
130                 135                 140

Val Asp Arg Tyr Phe Thr Ile Phe Tyr Ala Leu Gln Tyr His Asn Ile
145                 150                 155                 160

Met Thr Val Lys Arg Val Gly Ile Ser Ile Ser Cys Ile Trp Ala Ala
                165                 170                 175

Cys Thr Val Ser Gly Ile Leu Phe Ile Ile Tyr Ser Asp Ser Ser Ala
            180                 185                 190

Val Ile Ile Cys Leu Ile Thr Met Phe Phe Thr Met Leu Ala Leu Met
            195                 200                 205

Ala Ser Leu Tyr Val His Met Phe Leu Met Ala Arg Leu His Ile Lys
            210                 215                 220

Arg Ile Ala Val Leu Pro Gly Thr Gly Ala Ile Arg Gln Gly Ala Asn
225                 230                 235                 240

Met Lys Gly Ala Ile Thr Leu Thr Ile Leu Ile Gly Val Phe Val Val
                245                 250                 255

Cys Trp Ala Pro Phe Phe Leu His Leu Ile Phe Tyr Ile Ser Cys Pro
            260                 265                 270

Gln Asn Pro Tyr Cys Val Cys Phe Met Ser His Phe Asn Leu Tyr Leu
            275                 280                 285

Ile Leu Ile Met Cys Asn Ser Ile Ile Asp Pro Leu Ile Tyr Ala Leu
290                 295                 300

Arg Ser Gln Glu Leu Arg Lys Thr Phe Lys Glu Ile Ile Cys Cys Tyr
305                 310                 315                 320

Pro Leu Gly Gly Leu Cys Asp Leu Ser Ser Arg Tyr
                325                 330
```

(2) INFORMATION FOR SEQ ID NO:7:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

AATTAGCGGC CGCAGTATGC AAAAAAAGC CCGCTCATTA GGCGGGCT        48

(2) INFORMATION FOR SEQ ID NO:8:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

CCGAAGCCCG CCTAATGAGC GGGCTTTTTT TTGCATACTG CGGCCGCT        48

(2) INFORMATION FOR SEQ ID NO:9:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

```
GGCCGGCATG CATCAAGCTT ATCTCGAGAT CGTCGACTAC CATGGTACAT CGATCAGGTA      60

CCATCCCGGG GC                                                         72
```

(2) INFORMATION FOR SEQ ID NO:10:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

```
GGCCGCCCCG GGATGGTACC TGATCGATGT ACCATGGTAG TCGACGATCT CGAGATAAGC      60

TTGATGCATG CC                                                         72
```